(12) United States Patent
Hoon et al.

(10) Patent No.: US 7,910,295 B2
(45) Date of Patent: *Mar. 22, 2011

(54) DETECTION OF MICRO METASTASIS OF MELANOMA AND BREAST CANCER IN PARAFFIN-EMBEDDED TUMOR DRAINING LYMPH NODES BY MULTIMARKER QUANTITATIVE RT-PCR

(75) Inventors: Dave S. B. Hoon, Los Angeles, CA (US); Hiroya Takeuchi, Tokyo (JP)

(73) Assignee: John Wayne Cancer Institute, Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/713,808

(22) Filed: Nov. 14, 2003

(65) Prior Publication Data

US 2004/0265845 A1 Dec. 30, 2004

Related U.S. Application Data

(60) Provisional application No. 60/426,216, filed on Nov. 14, 2002.

(51) Int. Cl.
*C12Q 1/68* (2006.01)
(52) U.S. Cl. .......................................................... 435/6
(58) Field of Classification Search ................ 435/6, 7.1
See application file for complete search history.

(56) References Cited

U.S. PATENT DOCUMENTS

| | | | |
|---|---|---|---|
| 6,057,105 A * | 5/2000 | Hoon et al. ................. | 435/6 |
| 6,248,535 B1 | 6/2001 | Danenberg et al. ........... | 435/6 |
| 6,331,393 B1 | 12/2001 | Laird et al. ................ | 435/6 |
| 6,428,963 B2 | 8/2002 | Danenberg et al. ........... | 435/6 |
| 6,518,416 B1 | 2/2003 | Danenberg ............. | 536/24.33 |
| 6,573,052 B2 | 6/2003 | Danenberg ................... | 435/6 |
| 6,602,670 B2 | 8/2003 | Danenberg ................... | 435/6 |
| 6,610,488 B2 | 8/2003 | Danenberg et al. ........... | 435/6 |
| 6,613,518 B2 | 9/2003 | Danenberg et al. ........... | 435/6 |
| 2001/0029018 A1* | 10/2001 | Danenberg et al. ........... | 435/6 |

FOREIGN PATENT DOCUMENTS

| | | |
|---|---|---|
| EP | 0 520 794 A1 | 6/1992 |
| WO | 96/29430 A | 9/1996 |
| WO | WO 99/10528 | 3/1999 |
| WO | WO 02/70571 | 3/2002 |
| WO | 2004/045521 A | 6/2004 |

OTHER PUBLICATIONS

Kuo et al (Feb. 1998, Clinical Cancer Research, 4:411-418).*
Palmieri et al (Mar. 2001, Journal of Clinical Oncology, 19(5):1437-1443).*
Scholl et al (Feb. 2001, Cancer Research, 61:823-826).*
Koyanagi et al (2005) J Clin Oncol 23(31):8057-8064.*
Tockman et al (Cancer Res., 1992, 52:2711s-2718s).*
Koyanagi et al (J Clin Oncol, 2005, 23(31):8057-8064).*
Johansson et al (2000, Clinical Chemistry, 46(7): 921-927).*
Hatta et al (Melanoma Research, Aug. 1999, 9(4): abstract).*
Scoggins et al (Journal of Clinical Oncology, 2006, 24(18): 2849-2857).*
Mocellin et al (TRENDS in Molecular Medicine, 2003, 9(5):189-195).*
Tsao et al (Arch Dermatol, 2001, 137:325-330).*
Gerber et al (Journal of Clinical Oncology, 2001, 19(4): 960-971).*
Hilari et al (Ann Surg Oncol, 2009, 16(1): 177-185).*
Tatilidil et al (Modern Pathology, 2007, 20: 427-434).*
Denninghoff et al (Mol Diag, 2004, 8(4): Abstract).*
Hoon et al (J Clin Oncol, 1995, 13(18): 2109-2116).*
Scoggins et al (Journal of Clinical Oncology, 2006, 24(16):2849-2856).*
Hillari et al (Ann Surg Oncol, 2009, 16:177-185).*
Kuo et al (Clinical Cancer Research, 1998, 4(411-418).*
Morton, D. L., Wen, D. R., Wong, J. H., Economou, J. S., Cagle, L. A., Storm, F. K., et al. Techinical details of intraoperative lymphatic mapping for early stage melanoma. Arch Surg 127:392-399, 1992.
Li W, Stall A, Shivers SC, Lin J, Haddad F, Messina J, et al. Clinical relevance of molecular staging for melanoma: comparison of RT-PCR and immunohistochemistry staining in sentinel lymph nodes of paients with melanoma. Ann Surg 2000;231:795-803.
Hoon DS, Wang Y, Dale PS, Conrad AJ, Schmid P, Garrison D, Kuo CK, Foshag LJ, Nizze JA., Morton DL. Detection o occult melanoma cells in blood with a multiple-marker polymerase chain reaction assay. J. Clin. Oncol., 13: 2109-16, 1995.
Morton DL, Wen DR, Foshag LJ, Essner R, Cochran A. Intraoperative lymphatic mapping and selective cervical lymphadenectomy for early-stage melanomas of the head and neck. J Clin Oncol 1993;11:1751-6.
Morton DL, Thompson JF, Essner R, Elashoff R, Stern SL, Nieweg OE, et al. Validation of the accuracy of intraoperative lymphatic mapping and sentinel lymphadenectomy for early-stage melanoma: multicenter trial. Multicenter Selective Lymphadenectomy Trial Group. Ann Surg 1999;230:453-63. Taback B, Morton DL, O'Day SJ, Nguyen Dh, Nakayama T, Hoon DS. The clinical utility of multimarker RT-PCR in the detection of occult metastasis in patients with melanoma. Recent Results. Cancer Res 2001;158:78-92.
Sarantou, T., Chi, D. D. J., Garrison, D. A., Conrad, A.J., Schmid, P. Morton, D. L., and Hoon D. S. B. Melanoma-associated antigens as messenger RNA detection markers for melanoma. Cancer Res., 57: 1371-1376, 1997.

(Continued)

Primary Examiner — Sean E Aeder
(74) Attorney, Agent, or Firm — Brooks Kushman P.C.

(57) ABSTRACT

The invention provides a quantitative realtime RT-PCR assay for detection of metastatic breast, gastric, pancreas or colon cancer cells or metastatic melanoma. The assay allows to predict disease recurrence and survival in patients with AJCC stage I and II, and III disease using multimarker panels. The method for detecting metastatic melanoma cells utilizes panels of markers selected from a group consisting of MAGE-A3, GalNAcT, MART-1, PAX3, Mitf, TRP-2, and Tyrosinase. The method for detecting metastatic breast, gastric, pancreas or colon cancer cells in paraffin-embedded samples utilizes panels of markers selected from a group consisting of C-Met, MAGE-A3, Stanniocalcin-1, mammoglobin, HSP27, GalNAcT, CK20, and β-HCG.

18 Claims, 6 Drawing Sheets

OTHER PUBLICATIONS

Bostick, P. J., Morton, D. L., Turner, R. R., Huynh K. T., Wang, H-J., Elashoff R., Essner R., and Hoon, D. S. B Prognostic significance of occult metastases detected by sentinel lymphadenectomy and reverse transcriptase-polymerase chain reaction in early-stage melanoma patients. J. Clin. Oncol, 17: 3238-3244, 1999.

Hoon D. S. B, Bostick P., Kuo, C., Okamoto T, Wang H-J., Elashoff, R., and Morton, D. L. Molecular markers in blood a surrogate prognostic indicators of melanoma recurrence. Cancer Res., 60: 2253-2257, 2000.

Miyashiro, I., Kuo, C., Huynh, K., Iida A., Morton D., Bilchik, A., Giuliano A., and Hoon D. S. B. Molecular strategy fo detecting metastatic cancers with use of multiple tumor-specific MAGE-A genes. Clin. Chem. 47: 505-512, 2001.

Masuda N, Ohnishi T, Kawamoto S, Monden M, Okubo K. Analysis of chemical modification of RNA from formalin-fix samples and optimization of molecular biology applications for such samples. Nuc Acid Res 1999;27:4436-43.

Shirota Y, Stoehlmacher J, Brabender J, et al. ERCC1 and thymidylate synthase mRNA levels predict survival for colorectal cancer patients receiving combination oxaliplatin and fluorouracil chemotherapy. J Clin Oncol 2001;19:4298 304.

Hoon DS, Banez M, Okun E, Morton DL, Irie RF. Modulation of human melanoma cells by interleukin-4 and in combination with γ-interferon or α-tumor necrosis factor. Cancer Res 1991;51:2002-8.

Tai T, Paulson JC, Cahan LD, Irie RF. Ganglioside GM2 as a human tumor antigen (OFA-I-1). Proc Natl Acad Sci US 1983;80:5392-6.

Kuo CT, Bostick PJ, Irie RF, Morton DL, Conrad AJ, Hoon DS. Assessment of messenger RNA of β 1→4-N-acetylgalactosaminyl-transferase as a molecular marker for metastatic melanoma. Clin Cancer Res 1998;4:411-8.

Morton DL, Barth A. Vaccine therapy for malignant melanoma. CA Cancer J Clin 1996;46:225-44.

O'Day SJ, Boasberg PD, Piro L, Kristedja TS, et al. Maintenance biotherapy for metastatic melanoma with interleukin 2 and granulocyte macrophage-colony stimulating factor improves survival for patients responding to induction concurrent biochemotherapy. Clin Cance Res 2002;8:2775-81.

Henderson AR. Assessing test accuracy and its clinical consequences: a primer for receiver operating characteristic curve analysis. Ann Clin Biochem 1993;30:521-29.

Mitas M, Mikhitarian K, Walters C, et al. Quantitative real-time RT-PCR detection of breast cancer micrometastasis using a multigene marker panel. Int J Cancer 2001;93:162-71.

Bilchik, A. J., Saha, S., Wiese, D., Stonecypher, J. A., Wood, T. F., Sostrin, S., Turner, R. R., Wang, H-J., Morton D. L., and Hoon, D. S. B Molecular staging of early colon cancer on the basis of sentinel node analysis: A multicenter phase I trial. J. Clin. Oncol, 19: 1128-1136, 2001.

Bilchek et al., "Molecular Detection of Metastatic Pancreatic Carcinoma Cells Using a Multimarker Reverse Transcriptase-Polymerase Chain Reaction Assay". Cancer. 88:1037-1044 (2000).

Supplementary European Search Report (SESR).

Kocher et al., "Identification of Genes Differentially Expressed in Melanoma Sublines Derived from a Single Surgical Specimen Characterized by Different Sensitivity to Cytotoxic T-lymphocyte Activity," Dept. of Surgery, Z.L.F., pp. 617-624.

Vachtenheim et al., "Expression of Genes for Microphthalmia Isoforms, PAX3 and MSG1, in Human Melanomas," Cellular and Molecular Biology, vol. 45, pp. 1075-1082 (1999).

Balch et al., "Final Version of the American Joint Committee on Cancer Staging System for Cutaneous Melanoma," J. Clin. Oncol., 19: 3635-48, 2001.

Balch et al., "New TNM Melanoma Staging System: Linking Biology and Natural History to Clinical Outcomes," Semin. Surgical Oncology, 21: 43-52, 2003.

Bostick et al., "Limitations of Specific Reverse-Transcriptase Polymerase Chain Reaction Markers in the Detection of Metastases in the Lymph Nodes and Blood of Breast Cancer Patients," J. Clinical Oncol., 16: 2632-40, 1998.

Bouras et al., "Stanniocalcin 2 is an Enstrogen-Responsive Gene Coexpressed with the Estrogen Receptor in Human Breast Cancer," Cancer Res., 62: 1289-95, 2002.

Bustin, "Absolute Quantification of mRNA Using Real-Time Reverse Transcription Polymerase Chain Reaction Assay," J. of Molecular Endocrinology, 25: 169-93, 2000.

Chang et al., "Mammalian Stanniocalcins and Cancer," Endocrine-Related Cancer, v. 10: 359-373, 2003.

Choi et al., "Comparison of Tyrosinase-Related Protein-2, S-100, and Melan A Immunoreactivity in Canine Amelanotic Melanomas," Vet. Pathology, 40: 713-718, 2003.

Coulie et al., "A Monoclonal Cytolytic T-Lymphocyte Response Observed in a Melanoma Patient Vaccinated with a Tumor-Specific Antigen Peptide Encoded by Gene MAGE-3," PNAS, v. 98, pp. 10290-10295, 2001.

Cristofanilli et al., "Circulating Tumor Cells, Disease Progression, and Survival in Metastatic Breast Cancer," N. England J. Med., 351: 781-91, 2004.

Gaugler et al., "Human Gene MAGE-3 Codes for an Antigen Recognized on a Melanoma by Autologous Cytolytic T. Lymphocytes," J. Exp. Med., 179: 921-30, 1994.

Glaser et al., "Detection of Circulating Melanoma Cells by Specific Amplification of Tyrosinase Complementary DNA is not a Reliable Tumor Marker in Melanoma Patients: A Clinical Two-Center Study," J. Clinical Oncol., 15: 2818-25, 1997.

Goding, "Mitf from Neural Crest to Melanoma: Signal Transduction and Transcription in the Melanocyte Lineage," Genes Dev. 14: 1712-28, 2000.

Gradilone et al., "Detection of CK19, CK20 and EGFR mRNAs in Peripheral Blood of Carcinoma Patients: Correlation with Clinical Stage of Disease," Oncology Reports, v. 10: 217-222, 2003.

Irie et al., "Human Monoclonal Antibody to Gaglioside GM2 for Melanoma Treatment," Lancet 1: 786-7, 1989.

Jung et al., "Evaluation of Tyrosinase mRNA as a Tumor Marker in the Blood of Melanoma Patients," J. Clinical Oncol., 15: 2826-31, 1997.

Kawakami et al., "Cloning of the Gene Coding for a Shared Human Melanoma Antigen Recognized by Autologous T Cells Infiltrating Into Tumor," Proc. Nat'l. Acad. Sci. USA, 91: 3515-9, 1994.

Kawakami et al., "Identification of the Immunodominant Peptides of the MART-1 Human Melanoma Antigen Recognized by the Majority of HLA-A2-Restriction Tumor Infiltrating Lymphocytes," J. Exp. Med., 180: 347-52, 1994.

Keilholz, Ulrich et al., "Quantitative Detection of Circulating Tumor Cells in Cutaneous and Ocular Melanoma and Quality Assessment by Real-time Reverse Transcriptase-Polymerase Chain Reaction," Clinical Cancer Research, v. 10, Mar. 1, 2004, pp. 1605-1612.

Koyanagi et al., "Multimarker Quantitative Real-Time PCR Detection of Circulating Melanoma Cells in Peripheral Blood: Relation to Disease Stage in Melanoma Patients," Clinical Chem., 51: 981-8, 2005.

Marchetti et al., "mRNA Markers of Breast Cancer Nodal Metastases: Comparison Between Mammaglobin and Carcinoembryonic Antigen in 248 Patients," J. Pathology, v. 195, 186-190, 2001.

Marincola et al., "Escape of Human Solid Tumors from T-Cell Recognition: Molecular Mechanisms and Functional Significance," Adv. Immunol. 74: 181-373, 2000.

Pantel et al., "Detection and Clinical Importance of Micrometastatic Disease," J. Nat'l. Cancer Inst., 91: 113-24, 1999.

Peng et al., "Multiple PCR Analyses on Trace Amounts of DNA Extracted from Fresh and Paraffin Wax Embedded Tissues After Random Hexamer Primer PCR Amplification," J. Clinical Pathology, v. 47, pp. 605-608, 1994.

Zehentner et al., Mammaglobin as a Novel Breast Cancer Biomarker: Multigene Reverse Transcription-PCR Assay and Sandwich ELISA, Clinical Chemistry, 50: 2069-76, 2004.

Schultz et al., "A MAGE-A3 Peptide Presented by HLA-DP4 is Recognized on Tumor Cells by CD4+ Cytolytic T Lymphocytes," Cancer Research, 60: 6272-5, 2000.

Schuster, R. et al., "Quantitative Real-Time RT-PCR for Detection of Disseminated Tumor Cells in Peripheral Blood of Patients with Colorectal Cancer Using Different mRNA Markers," Ins. J. Cancer, v. 108, n. 2, pp. 219-227, Jan. 10, 2004.

Soong et al., "Quantitative Reverse Transcription-Polymerase Chain Reaction Detection of Cytokeratin 20 in Noncolorectal Lymph Nodes," Clinical Cancer Res., v. 7, 3423-3429, 2001.

Sorensen, B.S. et al., "Quantification of Melanoma Cell-specific MART-I mRNA in Peripheral Blood by a Calibrated Competitive Reverse Transcription-PCR," Clinical Chemistry 46:12, Sep. 26, 2000, pp. 1923-1928.

Stathopoulou et al., "Real Time Quantification of CK-19 mRNA-Positive Cells in Peripheral Blood of Breast Cancer Patients Using the Lightcycler System," Clinical Cancer Research, 9: 5145-5151, 2003.

Taback et al., "Detection of Occult Metastatic Breast Cancer Cells in Blood by a Multimolecular Marker Assay: Correlation with Clinical Stage of Disease," Cancer Research, 61: 8845-8850, 2001.

Takeuchi et al., "Expression of Differentiation Melanoma-Associated Antigen Genes is Associated with Favorable Disease Outcome in Advanced-Stage Melanomas," Cancer Research, 63: 441-8, 2003.

Takeuchi et al., "Prognostic Significance of Molecular Upstaging of Paraffin-Embedded Sentinel Lymph Nodes in Melanoma Patients," J. Clinical Oncology, 22: 2671-80, 2004.

Voit et al., "Molecular Staging in Stage II and III Melanoma Patients and its Effect on Long-Term Survival," J. Clinical Oncology, 23: 1218-1227, 2005.

Wascher et al., "Molecular Tumor Markers in the Blood: Early Prediction of Disease Outcome in Melanoma Patients Treated with a Melanoma Vaccine," J. Clinical Oncology, 21:2558-63, 2003.

Wascher et al., "Stannicalcin-1: A Novel Molecular Blood and Bone Marrow Marker for Human Breast Cancer," Clinical Cancer Res., 9: 1427-35, 2003.

Balch et al., "Efficacy of an Elective Regional Lymph Node Dissection of 1 to 4 mm Thick Melanomas for Patients 60 Years of Age and Younger," Ann. Surg. 1996; 224:255-63.

Balch et al., A Comparison of Prognostic Factors and Surgical Results in 1,786 Patients with Localized (stage I) Melanoma Treated in Alabama, USA and New South Wales, Australia, Ann. Surg. 196:677-684, 1982.

Cascinelli et al., "Immediate or Delayed Dissection of Regional Nodes in Patients with Melanoma of the Trunk: a Randomized Trail," WHO Melanoma Programme. Lancet, 1998; 351:796-6.

Clegg, R.M., "Fluorescence Energy Transfer.," Curr. Opin. Biotech, 6: 103-110, 1995.

Cochran et al., "Occult Melanoma in Lymph Nodes Detected by Antiserum to S-100 Protein," Int. J. Cancer, 1984; 34:159-63.

Jemal et al., Cancer Statistics 2002, CA Cancer J. Clin., 52: 23-47, 2002.

Kawakami et al., "Identification of a Human Melanoma Antigen Recognized by Tumor-Infiltrating Lymphocytes Associated with In Vivo Tumor Rejection," Proc. Natl. Acad. Sci., USA, 91: 6458-6462, 1994.

Morton et al., "Prolongation of Survival in Metastatic Melanoma After Active Specific Immunotherapy with a New Polyvalent Melanoma Vaccine," Ann. Surg. 1992; 216:463-82.

Rigel et al., "The Incidence of Malignant Melanoma in the United States: Issues as we Approach the 21st Century," J. Am. Acad. Dermotol., 34: 839-847, 1996.

Shivers et al., "Molecular Staging of Malignant Melanoma: Correlation with Clinical Outcome," JAMA 1998; 280:1410-5.

Final Version of the American Joint Committee on Cancer Staging System for Cutaneous Melanoma, J. Clin. Oncol., 16: 3635-3648, 2001.

Specht, K. et al., "Quantitative Gene Expression Anaylsis in Microdissected Archival Tissue by Real-Time RT-PCR," J. Mol. Med. 78:B27, 2000 (Abstract).

* cited by examiner

SEQUENCE LISTING

```
<160> NUMBER OF SEQ ID NOS: 15

<210> SEQ ID NO 1
<211> LENGTH: 24
<212> TYPE: DNA
<213> ORGANISM: Artificial
<220> FEATURE:
<223> OTHER INFORMATION: Synthetic oligonucleotide

<400> SEQUENCE: 1
cagaacagtc accaccacct tatt                                        24

<210> SEQ ID NO 2
<211> LENGTH: 25
<212> TYPE: DNA
<213> ORGANISM: Artificial
<220> FEATURE:
<223> OTHER INFORMATION: Synthetic oligonucleotide

<400> SEQUENCE: 2
agctcctgcc cacactcccg cctgt                                       25

<210> SEQ ID NO 3
<211> LENGTH: 24
<212> TYPE: DNA
<213> ORGANISM: Artificial
<220> FEATURE:
<223> OTHER INFORMATION: Synthetic oligonucleotide

<400> SEQUENCE: 3
atgaggctgc tttcactatc cgca                                        24

<210> SEQ ID NO 4
```

```
<211> LENGTH: 23
<212> TYPE: DNA
<213> ORGANISM: Artificial
<220> FEATURE:
<223> OTHER INFORMATION: Synthetic oligonucleotide

<400> SEQUENCE: 4
ccagactgat tacgcgctct ccc                                           23

<210> SEQ ID NO 5
<211> LENGTH: 24
<212> TYPE: DNA
<213> ORGANISM: Artificial
<220> FEATURE:
<223> OTHER INFORMATION: Synthetic oligonucleotide

<400> SEQUENCE: 5
cagcaatgcc tcctgcacca ccaa                                          24

<210> SEQ ID NO 6
<211> LENGTH: 23
<212> TYPE: DNA
<213> ORGANISM: Artificial
<220> FEATURE:
<223> OTHER INFORMATION: Synthetic oligonucleotide

<400> SEQUENCE: 6
agagcactgg ccaaagagag gca                                           23

<210> SEQ ID NO 7
<211> LENGTH: 25
<212> TYPE: DNA
<213> ORGANISM: Artificial
<220> FEATURE:
<223> OTHER INFORMATION: Synthetic oligonucleotide

<400> SEQUENCE: 7
tcacatcaag gacctgcatt tgtta                                         25

<210> SEQ ID NO 8
<211> LENGTH: 26
<212> TYPE: DNA
<213> ORGANISM: Artificial
<220> FEATURE:
<223> OTHER INFORMATION: Synthetic oligonucleotide

<400> SEQUENCE: 8
ttcaccatgc atttgttgac agtatt                                        26

<210> SEQ ID NO 9
<211> LENGTH: 22
<212> TYPE: DNA
<213> ORGANISM: Artificial
<220> FEATURE:
<223> OTHER INFORMATION: Synthetic oligonucleotide

<400> SEQUENCE: 9
tgggagctga tgacaagagg ag                                            22

<210> SEQ ID NO 10
<211> LENGTH: 24
<212> TYPE: DNA
<213> ORGANISM: Artificial
<220> FEATURE:
<223> OTHER INFORMATION: Synthetic oligonucleotide

<400> SEQUENCE: 10
```

```
cctgctggaa tgtgatgaag acac                                          24

<210> SEQ ID NO 11
<211> LENGTH: 18
<212> TYPE: DNA
<213> ORGANISM: Artificial
<220> FEATURE:
<223> OTHER INFORMATION: Synthetic oligonucleotide

<400> SEQUENCE: 11
cactgctacg caggctct                                                 18

<210> SEQ ID NO 12
<211> LENGTH: 18
<212> TYPE: DNA
<213> ORGANISM: Artificial
<220> FEATURE:
<223> OTHER INFORMATION: Synthetic oligonucleotide

<400> SEQUENCE: 12
tgctcagagt ttcatccg                                                 18

<210> SEQ ID NO 13
<211> LENGTH: 20
<212> TYPE: DNA
<213> ORGANISM: Artificial
<220> FEATURE:
<223> OTHER INFORMATION: Synthetic oligonucleotide

<400> SEQUENCE: 13
aggagcggca ggacgagcat                                               20

<210> SEQ ID NO 14
<211> LENGTH: 25
<212> TYPE: DNA
<213> ORGANISM: Artificial
<220> FEATURE:
<223> OTHER INFORMATION: Synthetic oligonucleotide

<400> SEQUENCE: 14
atcagttaag caccctggaa gagag                                         25

<210> SEQ ID NO 15
<211> LENGTH: 22
<212> TYPE: DNA
<213> ORGANISM: Artificial
<220> FEATURE:
<223> OTHER INFORMATION: Synthetic oligonucleotide

<400> SEQUENCE: 15
cctgcctcag gtggtgtgca ac                                            22
```

DETECTION OF MICRO METASTASIS OF MELANOMA AND BREAST CANCER IN PARAFFIN-EMBEDDED TUMOR DRAINING LYMPH NODES BY MULTIMARKER QUANTITATIVE RT-PCR

This invention claims priority to the U.S. Provisional Patent Application No. 60/426,216 filed Nov. 14, 2002.

BACKGROUND OF THE INVENTION

The present invention relates to methods of detection of micro metastasis in lymph nodes and methods of predicting the recurrence of the disease and survival. More specifically, the invention is directed to detection of micro metastasis in cancerous tissue and lymph nodes by using multimarker real-time reverse transcriptase polymerase chain reaction assay.

DESCRIPTION OF THE PRIOR ART

The incidence of malignant melanoma has been increasing in the United States over the past decade (Balch, C. M., 2001; Jemal, A. J., 2002; and Rigel, D. S., 1996). Breast cancer is another common form of malignant disease whose incidence is increasing. One of the most devastating aspects of cancer is the propensity of cells from malignant neoplasms to disseminate from their primary site to distant organs and develop into metastases. Despite advances in surgical treatment of primary neoplasms and aggressive therapies, most cancer patients die as a result of metastatic disease.

Cancers are staged according to a well-defined, elaborate progressive scale, developed by the American Joint Committee on Cancer (AJCC). Caught early, cancer is very often curable. The five-year survival rate varies considerably depending on the AJCC stage level. For example, for Stage I and Stage II melanoma, the five-year survival rate is over 80%. However, for Stage IV the survival rate is less that 20% (AJCC). Similarly, the overall five-year breast cancer survival rate is about 75 percent for white women and about 63 percent for black women. This rate rises to nearly 90 percent for women with Stage I or II cancer (U.S. Pat. No. 6,057,105, which is incorporated herein by the reference). Therefore, accurate determination of an AJCC stage is extremely important for selecting patients for adjuvant therapies and for directing follow-up procedures.

Until recently, a complete dissection of regional lymph nodes was performed to obtain nodal staging information. All lymph nodes of the lymphatic drainage basin were removed for pathology examination for the presence of micrometastases (Balch, C. M., 1996; Cascinelli, N., 1998; Li, W., 1999). However, such approach is labor-intensive. Also, about 80% of patients who undergo elective lymph node dissection have no evidence of metastases and do not benefit from this procedure.

John Wayne Cancer Institute (JWCI) has pioneered an alternative sentinel lymphadenectomy (SLND) technique for the treatment of early stage melanoma (Morton, D. L., 1992; Morton, D. L., 1993; Morton, D. L., 1999). Sentinel lymph node (SLN) is defined as the first lymph node in the regional lymphatic basin that drains the primary tumor. Several reports have confirmed that the SLN is the first node that receives metastatic melanoma cells and that the SLN reflects the metastatic status of the entire lymphatic basin (Morton, D. L., 1992; Li, W., 1999). Conceptually, a tumor-negative SLN predicts the absence of tumor metastases in the other regional lymph nodes (non-SLN) with a high degree of accuracy. Typically, the probability of non-SLN in the draining lymphatic basin containing melanoma cells is less than 1% when the SLN does not have metastatic melanoma cells (Morton, D. L., 1992). Thus, in the case of a tumor-negative SLN, this method allows to avoid complete lymph node dissection and various postoperative complications associated with such procedure.

Standard procedure for the histopathologic examination of regional lymph nodes utilizes hematoxylin and eosin (H&E) staining. But this procedure often underestimates the presence of micrometastatic disease. Immunohistochemistry (IHC) staining with HMB-45 and S-100 antibodies can increase the sensitivity of detecting melanoma cells in lymph nodes tenfold over H&E staining alone (Bostick, P. J., 1999; Cochran, A. J., 1984; Shivers, S. C., 1998; Li, W., 1999).

Development of reverse transcriptase polymerase chain reaction (RT-PCR) assays and gene markers for different tumor types, such as tyrosinase for melanoma, made it possible to detect occult metastases in lymph nodes of cancer patients whose disease was not found by either H&E or IHC techniques (Li, W., 2000). Despite initially encouraging results, the clinical and survival significance of these occult metastases detected by RT-PCR assays has not been demonstrated conclusively. Furthermore, conventional single mRNA marker RT-PCR assays are limited in their ability to discriminate cancer cells from normal cells that also carry the marker and, thus, these methods suffer from reduced specificity and reliability. In addition, tumor heterogeneity has caused sensitivity problems where a single mRNA marker was employed—although all tumor cells within a primary tumor or metastasis may express the same marker gene, the level of specific mRNA expression can vary considerably. Thus, despite the identification of melanoma and breast cancer markers, these markers cannot individually detect tumor cells in a highly specific and sensitive manner (U.S. Pat. No. 6,057,105).

A multimarker RT-PCR assay eliminates some of the problems associated with single-marker detection techniques. To date, several multiple-mRNA marker (MM) RT-PCR assays have been developed for detecting occult metastatic melanoma cells in blood, bone marrow, or lymph nodes (Taback, B., 2001; Sarantou, T., 1997; Bostick, P. J., 1999; Hoon, D. S. B., 2000; Miyashiro, I., 2001). For example, a marker combination of tyrosinase and melanoma-associated antigens MART-1 and MAGE-A3 have been used to detect occult melanoma cells in frozen sections of SLNs (Bostick, P. J., 1999). Although this study reported a great improvement of detection sensitivity compared to H&E staining and IHC, the study did not determine clinicopathologic importance of the detection. Also, since the study limited the follow-up period to 12 months and recurrence of melanoma, typically, takes 3-8 years, it failed to establish an ability of the selected markers to predict disease recurrence and patient's overall survival.

A panel of three tumor mRNA markers, beta-chain human chorionic gonadotropin (β-hCG), hepatocyte growth factor (C-Met), and universal MAGE (uMAGE) was used in a combination with RT-PCR to detect nodal micrometastases of colorectal cancer. But the study did not establish the prognostic significance of the method (Bilchik, A. J., 2000).

The U.S. Pat. No. 6,057,105 describes an RT-PCR method of detecting metastatic melanoma cells with a set of melanoma marker genes, including tyrisonase, MART-1, tyrosinase related protein-1 (TRP-1), and MAGE-A3. The patent also describes an RT-PCR method of detecting breast cancer cells with a set of marker genes, including C-Met, glycosyl-transferase β-1,4-N-acetylgalacto-saminyltransferase (GalNAcT), β-hCG, MAGE-A3, MAGE-2, and Cytokeratin-20

(CK20). Although the methods of the U.S. Pat. No. 6,057,105 are more sensitive than RT-PCR with a single marker, they fail to predict a long-term (at least 3 years) disease recurrence and survival.

The U.S. Pat. No. 6,037,129 describes an RT-PCR method of detecting metastatic breast cancer cells with a set of marker genes, including c-Myc, PIP, and keratin-19. This patent utilizes regression analysis to determine a correlation between number of positive RT-PCR markers and predicted survival per AJCC stage. However, similarly to the U.S. Pat. No. 6,057,105, the U.S. Pat. No. 6,037,129 does not conduct a retrospective long-term (greater than 5 years) analysis of the samples and, thus, does not evaluate prognostic significance of the selected markers. Also, the selected set of the markers has a limited utility as it produced a large number (40%) of false positive results.

In summary, none of the currently available methods provides a reliable prediction of disease recurrence, patient's prognosis and survival, particularly in AJCC stage I, II and III patients.

SUMMARY OF THE INVENTION

In view of the described shortcomings of the existing methods for detection metastatic cancer cells, it is one object of the present invention to provide high sensitivity methods for detection of metastatic melanoma, breast cancer, gastric cancer, pancreas cancer, or colon cancer cells. It is another object of the present invention to provide a method for predicting disease recurrence within at least three-year period, preferably at least five-year period, following removal of the primary melanoma and SLND. It is also an object of the present invention to identify a panel of molecular markers that can detect micrometastasis in tumor draining lymph nodes (TDLN) and sentinel lymph node (SLN). It is also an object of the present invention to provide methods for identification of metastasis in TDLN/SLN that are histopathologically negative as determined by H&E staining and IHC.

These and other objects are achieved in a method of detecting metastatic melanoma cells in a patient. The method comprises (a) isolating nucleic acid from a biological sample obtained from the patient; (b) amplifying nucleic acid targets, if present, from a panel of marker genes, wherein the panel comprises GalNAcT, a transcription factor PAX3, or both; and (c) detecting the presence or absence of the nucleic acid targets. The panel may further comprise markers selected from a group consisting of MAGE-A3, GalNAcT, MART-1, PAX3, MITF, TRP-2, and Tyrosinase.

In one embodiment the panel comprises MAGE-A3, GalNAcT, MART-1, and PAX3. In another embodiment the panel comprises MART-1, GalNAcT, MITF, and PAX3. In further embodiment the panel comprises MART-1, TRP-2, GalNAcT, and PAX3. In still another embodiment the panel comprises Tyrosinase, MART-1, GalNAcT, and PAX3. MART-1 is a melanoma antigen on melanosomes; GalNAcT is a glycosysltransferase for synthesis of gangliosides GM2 and GD2; Tyrosinase is a melanogenesis pathway enzyme to make melanin; Tyrosinase-related protein-2 (TRP-2) is a melanogenesis pathway enzyme. MITF and PAX3 are transcription factors.

In one embodiment, the panel of mRNA markers is used in a combination with RealTime RT-PCR (qRT-PCR) assay. The nucleic acid may be isolated from paraffin-embedded (PE) melanoma tissues, frozen lymph nodes, and PE lymph nodes. Prior to the present invention there had been no evidence in the art that the described panels of markers are useful for predicting disease outcome.

In another aspect, the present invention provides a method of detecting metastatic breast, gastric, pancreas or colon cancer cells in a patient. The method comprises (a) isolating nucleic acid from PE cancerous tissues or PE lymph nodes of the patient; (b) amplifying nucleic acid targets, if present, from a panel of marker genes selected from a group consisting of C-Met, MAGE-A3, Stanniocalcin-1, mammoglobin, heat shock protein 27 (HSP27), GalNAcT, cytokeratin 20 (CK20), and beta chain-human chorionic gonadotrophin (β-HCG); and (c) detecting the presence or absence of the nucleic acid targets. In one embodiment, the panel of mRNA markers is used in a combination with RealTime RT-PCR (qRT-PCR) assay. Prior to the present invention there had been no evidence in the art that the described panels of markers when used to amplify nucleic acid isolated from PE cancerous tissues or PE lymph nodes are useful for predicting disease outcome.

The methods of the present invention are rapid, repeatable and quantitative. They were validated using 215 melanoma patients in retrospective analysis with greater than 5 years follow up, which is a minimum amount of follow up needed to verify the prognostic significance of disease outcome in early stage patients.

In a different aspect, the present invention provides a kit for use in detecting melanoma cells in a biological sample. The kit comprises pairs of primers for amplifying nucleic acids targets from a panel of marker genes, wherein the panel comprises GalNAcT, PAX3, or both, and containers for each of the pairs of primers.

The present invention provides a number of unexpected advantages. First, it allows to determine stages of the cancers more accurately as compared to the existing methods. The methods and kit of the present invention allow accurate determination of a need for further lymph node removal surgery and/or adjuvant treatment. Second, the present invention demonstrates the better reliability of molecular marker panels of the present invention in prediction of the disease outcome and recurrence as compared to conventional prognostic factors such as age, gender, Breslow thickness, Clark level, site, ulceration. The panels of the present invention provide an accurate prediction of disease recurrence in histopathology negative SLN ($p<0.0001$) and survival ($p<0.0001$). The methods of the present invention diagnose metastasis in SLN with high sensitivity and specificity.

The invention is defined in the appended claims and is described below in its preferred embodiments.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail.

FIG. 1 shows representative quantitative RealTime RT-PCR (qRT-PCR) analysis for MART-1 mRNA copy levels.

DETAILED DESCRIPTION OF THE PREFERRED EMBODIMENTS

Figure 1A:
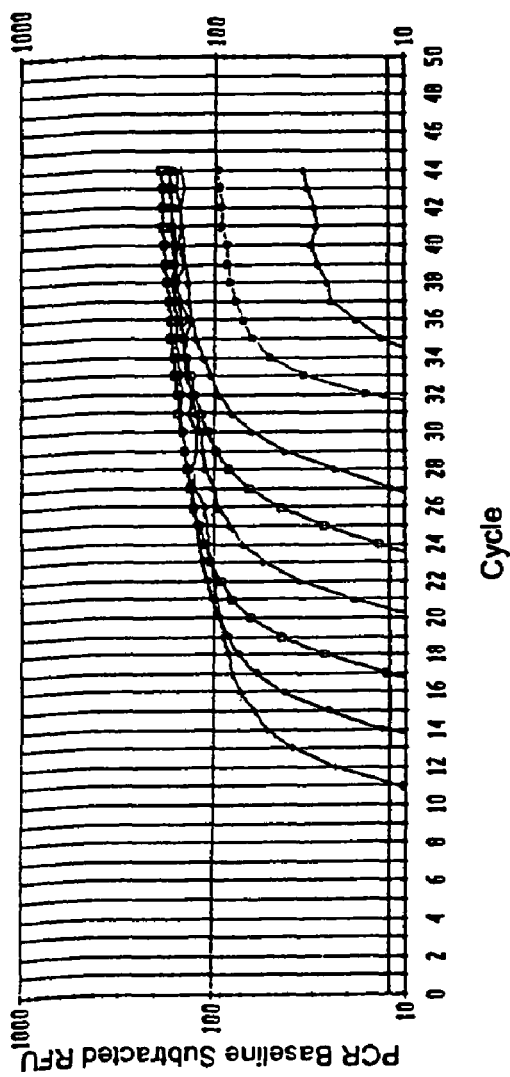
FIG. 1A depicts signal increase of the serially diluted plasmid containing MART-1 cDNA ($10^1$ to $10^8$ copies) standard templates with the increase of the number of PCR cycles. RFU is relative Fluorescence unit.

The present invention provides highly sensitive, multimarker methods to detect melanoma, breast, gastric, pancreas or colon cancer cells in SLNs of patients with or without clinical evidence of disease. The methods of the present invention are designed to overcome limitations in existing technologies with respect to sensitivity, specificity, and ability to predict outcome of the disease.

Recent studies have indicated that patients with histopathologically melanoma-free SLNs, who are positive for two or more mRNA markers as determined by RT-PCR, were at a significantly increased risk of recurrence compared with those who were positive for one or fewer mRNA markers (Bostick, P. J., 1999). However, because frozen tissue sections were used for these MM RT-PCR assays, a large number of SLN samples could not be assessed and large-scale retrospective analysis with a follow up of greater than three years could not be conducted. Accordingly, patient's survival under long term follow-up period could not be analyzed.

The instant invention solved this problem by utilizing paraffin-embedded (PE) specimens for MM RT-PCR assays to assess much larger patient population of SLN samples and analyze patient's longer follow-up survival data and to determine the significance of detection of molecular metastasis. One major advantage of the PE qRT-PCR assay is that retrospective analysis of specimens from multiple sources can be assessed and evaluated for clinicopathological utility.

Until recently, it was believed that mRNA cannot be preserved in PE tissues due to degeneration. It was also believed to be difficult to isolate mRNA from PE tissues for PCR analysis (Masuda, N., 1999; Shirota, Y., 2001). However, some recent investigations have proved the utility of RT-PCR assays using mRNA isolated from PE specimens (Masuda, N., 1999; Shirota, Y., 2001; Specht, K., 2000; U.S. Pat. No. 6,248,535; U.S. Pat. No. 6,602,670, all of which are incorporated herein by the reference). Additionally, the use of PE samples facilitates correlation of histopathological and RT-PCR data. This is because most of histopathological samples are prepared as formalin fixed and paraffin. These samples are retained in archival storage of a large number of pathology departments, along with their clinical histories and prognoses (U.S. Pat. No. 6,248,535; Masuda, N., 1999). Frozen sections are rarely, if ever, used for histopathology analysis. Additionally, frozen sections are logistically difficult to obtain and assess by RT-PCR.

In addition, recent development of RealTime RT-PCR (qRT-PCR) assay allows the rapid and reproducible quantitative analysis with high sensitivity and specificity. It is a high-throughput technology based on an online fluorescence detection system that allows sensitive detection and quantitation of gene expression (Shirota, Y., 2001). But even with these significant developments in the art, inability to predict recurrence of cancer after removal of the primary tumor remains to be a major problem.

In summary, the multi-marker panels of prior art, such as those of the U.S. Pat. No. 6,057,105, do not have a significant predictive power in disease recurrence. The marker panels of prior art that were created for frozen sections would not be predictive in PE samples. Earlier studies had at the most a twenty-month follow-up (Li, W., 2000) and could not evaluate the predictive power of markers for disease recurrence, which takes 3-8 years. Additionally, many of the markers utilized in earlier MM RT-PCRs were producing false-positive results (Li, W., 2000, U.S. Pat. No. 6,037,129).

The present invention solves these problems by providing a method of detecting metastatic melanoma cells in a patient. The method comprises (a) isolating nucleic acid from a biological sample of the patient; (b) amplifying nucleic acid targets, if present, from a panel of marker genes, wherein the panel comprises GalNAcT, PAX3, or both; and (c) detecting the presence or absence of the nucleic acid targets. The biological sample may be selected from a group consisting of PE melanoma tissues, frozen lymph nodes, and PE lymph nodes. The biological sample may be histopathologically negative or positive for melanoma cells. Typically, the histopathology of the biological sample is determined by hematoxylin and eosin staining or immunohistochemistry. However, other suitable methods can also be used.

The present invention unexpectedly demonstrates that GalNAcT and PAX3 are new promising molecular marker for detecting occult melanoma cells. By using a large well-defined patient population with a significant clinical follow up, the present invention unexpectedly demonstrated that the quantitative detection of these mRNA markers in SLNs in the patients with early-stage melanoma has clinicopathological and prognostic utilities.

GalNAcT is a key enzyme in the biosynthetic pathway of gangliosides GM2/GD2, which are oncofetal glycolipids found elevated in expression on the surface of melanomas (Hoon, D. S., 1991; Tai, T., 1983). In melanoma, gangliosides GM2 and GD2 expression, are often enhanced to very high levels and associated with tumor progression including metastatic tumors. Gangliosides are also highly expressed in breast cancer cells. The gangliosides GM2 and GD2 are immunogenic in humans and can be used as a target for specific immunotherapy such as human monoclonal antibodies or cancer vaccines (U.S. Pat. No. 6,057,105).

PAX3 transcription factor has been reported to regulate melanin synthetic pathway via MITF expression (Goding, C. R., 2000). PAX3 is well expressed in human melanomas and contributes to melanoma cell survival (Goding, C. R., 2000; Scholl, F. A., 2001). Recent studies have suggested the clinical usefulness of PAX3 gene expression as specific markers for detecting melanoma cells (Scholl, F. A., 2001).

In another embodiment of the present invention, the panel of markers may further comprise markers selected from a group consisting of MAGE-A3, GalNAcT, MART-1, PAX3, MITF, TRP-2, and Tyrosinase. MART-1 and MAGE-A3 are major melanocyte differentiation antigens that are immunogenic in patients and well expressed in melanoma (Kawakami, Y., 1994; Kawakami, Y., 1994; Marincola, F. M., 2000; Schultz, E. S., 2000). MAGE-A3 has high specificity and expression in melanoma cells (Sarantou, T., 1997; Miyashiro, I., 2001). Clinical utilities of assessing MAGE-A3 mRNA expression in primary tumor, metastatic lesion, and blood in melanoma patients have been previously reported (Miyashiro, I., 2001). Tyrosinase is a melanogenesis pathway enzyme to make melanin; Tyrosinase-related protein-2 (TRP-2) is a melanogenesis pathway enzyme. MITF is a transcription factor.

In one embodiment the panel comprises MAGE-A3, GalNAcT, MART-1, and PAX3. In another embodiment the panel comprises MART-1, GalNAcT, MITF, and PAX3. In further embodiment the panel comprises MART-1, TRP-2, GalNAcT, and PAX3. In still another embodiment the panel comprises Tyrosinase, MART-1, GalNAcT, and PAX3.

In one embodiment, mRNA expression levels of MART-1, MAGE-A3, GalNAcT, and PAX3 in PE SLNs were analyzed retrospectively using a qRT-PCR assay in 215 patients with early-stage melanoma. The study demonstrated the reliability of qRT-PCR assays with the selected panel of markers and using PE tissues of the large number (n=215) of patients with at least 5 yr follow-up after SLND. Previous research by the inventors has revealed that patients with histopathologically melanoma-free SLNs who were MM RT-PCR positive were at significantly increased risk of recurrence compared with those who were negative for mRNA markers (Bostick, P. J., 1999). However, the previous studies using frozen SLNs did not demonstrate the clinical usefulness of the assays and the selected marker sets because of the limitation of the number of patients and a shorter follow-up period after SLND.

The four mRNA markers of this embodiment are specific for and frequently found in melanomas (Sarantou, T., 1997; Miyashiro, I., 2001; Kawakami, Y., 1994; Kawakami, Y., 1994; Marincola, F. M., 2000; Schultz, E. S., 2000; Hoon, D. S., 1991; Tai, T., 1983; Kuo, C. T., 1998; Goding, C. R., 2000; Scholl, F. A., 2001). All four of the mRNA markers were expressed in 100% of melanoma cell lines. However, the mRNA copy number for individual markers vary in individual cell lines. Also, the mRNA copy levels in histopathology positive PE SLNs are not expressed in 100% but vary in individual SLNs. The results are due to not only the heterogeneity in individual tumor tissues but also the portion of micrometastases which have completely removed from the PE-block in some cases at the time of pathological examination (H&E and IHC), and also the quantity of the amount of mRNA for each sample.

In this embodiment of the present invention, at least one positive marker was identified in 89% of histopathologically positive SLNs demonstrating the accuracy of this study. MAGE-A3 alone was positive in 45% of positive SLNs. This result is compatible with a previous study in which MAGE-A3 mRNA was expressed in 43% of metastatic melanoma (Miyashiro, I., 2001). GalNAcT mRNA was expressed in 64% of histopathology positive SLNs. This result is consistent with earlier reported study (Kuo, C. T., 1998). PAX3 mRNA expression was identified from 77% of primary cultured melanoma but not identified from melanocyte using in situ hybridization (Scholl, F. A., 2001).

Among 162 histopathology negative SLN patients, 48 (30%) patients were upstaged by the (multi-marker panel (MM) qRT-PCR assay of the present invention. Interestingly, the increased number of expressed markers significantly correlated with worse disease-free survival (DFS) after SLND. By contrast, DFS and survival rate for the patients with no expression of any of the markers of the panel of the present invention was significantly high. Recurrence of the disease in patients who had no MM expression in SLNs may be due to the false-negative results by qRT-PCR assay or spread of disease through hematogeneous metastasis. In fact, eight (67%) of 12 patients who had no MM expression but recurred had hematogenic metastases as an initial recurrence site and the other four patients had lymphatic metastases at least 2 yr later after SLND.

The present invention demonstrate that when marker panels of the present invention are used, lack of expression of markers can predict favorable prognosis of the patients who had SLND. Interestingly, the mRNA copy number of each marker in patients who recurred was significantly higher than that in patients who did not recur among the histopathology negative SLN patients.

The qRT-PCR assays of the present invention not only provided qualitative but also quantitative data in predicting the patient's survival. Among the histopathology negative SLN patients, occult melanoma cells with higher MM copy levels correlate with disease recurrence. The present invention also demonstrates that histopathology negative and RT-PCR negative patients will remain disease-free and need less management.

The qRT-PCR assays of the present invention provides a rapid and reproducible approach with high sensitivity and specificity. Moreover, the assay does not require tedious and often subjective procedures required in detection of PCR products, such as in gel electrophoresis-based assays. The present invention demonstrates feasibility and utility of the MM qRT-PCR assays in PE samples by ROC curve analysis, comparison study between frozen and PE specimens of the same specimen, and dilution analysis using laser capture microdissection (LCM).

Accordingly, in one embodiment of the present invention, the panel of mRNA markers is used in a combination with qRT-PCR assay. It is a discovery of the present invention that the use of qRT-PCR in a combination with the panel of markers of the present invention greatly improves assay sensitivity and specificity for the detection of occult metastases in PE SLNs, which are H&E and IHC negative, and predict disease outcome in patients with early stage melanoma.

Accordingly, in one embodiment, the method for detecting metastatic cells of the present invention comprises a step of assigning an AJCC (American Joint Committee on Cancer) stage to the patient based on the presence or absence of the nucleic acid targets in the sample. In another embodiment, the method for detecting metastatic cells comprises a step of predicting at least one parameter selected from a group consisting of disease recurrence, patient's prognosis, and patient's survival, wherein the parameters are determined based on the presence or absence of the nucleic acid targets in the sample. Preferably, the parameter is predicted for at least three-year period following a removal of a primary tumor, sentinel lymphadenectomy (SLND), or both. The method may further comprise a step of selecting a treatment regimen based on the patient's prognosis.

It is also a discovery of the present invention that quantitative multiple marker expression in the PE SLN may more accurately reflect occult metastases of melanoma and be a more powerful predictor of patients' disease relapse and postoperative survival than H&E and IHC. Prior to the present invention there had been no evidence in the art that the described panels of markers are useful for predicting disease outcome. Accordingly, in another aspect, the present invention provides a method for detecting metastatic melanoma cells in PE samples. The method comprises (a) deparaffinizing PE melanoma tissue samples or PE lymph node samples to obtain deparaffinized samples; (b) isolating nucleic acid from the deparaffinized samples; (c) amplifying nucleic acid targets, if present, from a panel of marker genes, wherein the panel comprises at least two marker genes selected from a group consisting of MAGE-A3, GalNAcT, MART-1, PAX3, MITF, TRP-2, and Tyrosinase; and (d) detecting the presence or absence of the nucleic acid targets.

In another aspect, the present invention provides a method of detecting metastatic breast, gastric, pancreas or colon cancer cells in a patient. The method comprises (a) isolating nucleic acid from PE cancerous tissues or PE lymph nodes of the patient; (b) amplifying nucleic acid targets, if present, from a panel of marker genes selected from a group consisting of C-Met, MAGE-A3, Stanniocalcin-1, mammoglobin, heat shock protein 27 (HSP27), GalNAcT, cytokeratin 20 (CK20), and beta chain-human chorionic gonadotrophin (β-HCG); and (c) detecting the presence or absence of the nucleic acid targets.

C-Met is a cell surface receptor for hepatocyte growth factor (motility, growth, migration activation). MAGE-A3 is of unknown function. Characterized as an immunogenic antigen in human found in different cancers not normal tissue except testes and placenta. Sanniocalcin-1 is of unknown function in humans. Found in animals and fish to regulate calcium and phosphate levels. Mammoglobulin is related to secretions of the mammary gland. HSP 27 is a regulator of various cellular functions including apoptosis and is activated in malignancy. Cytokeratin 20 is cytoskeleton protein regulating shape and motility. Beta-HCG is a gonadotropin hormone that binds to beta-HCG receptor and is involved in growth and metabolic activation of a cell.

In one embodiment, the panel of mRNA markers is used in a combination with RealTime RT-PCR (qRT-PCR) assay. Prior to the present invention there had been no evidence in the art that the described panels of markers when used to amplify nucleic acid isolated from PE cancerous tissues or PE lymph nodes are useful for predicting disease outcome.

Accordingly, in one embodiment, the method for detecting metastatic breast, gastric, pancreas or colon cancer cells of the present invention comprises a step of assigning an AJCC (American Joint Committee on Cancer) stage to the patient based on the presence or absence of the nucleic acid targets in the sample. In another embodiment, the method for detecting metastatic cells comprises a step of predicting at least one parameter selected from a group consisting of disease recurrence, patient's prognosis, and patient's survival, wherein the parameters are determined based on the presence or absence of the nucleic acid targets in the sample. Preferably, the parameter is predicted for at least three-year period following a removal of a primary tumor, sentinel lymphadenectomy (SLND), or both. The method may further comprise a step of selecting a treatment regimen based on the patient's prognosis.

In a different aspect, the present invention provides kits for use in detecting melanoma cells in a biological sample. All the basic essential materials and reagents required for detecting melanoma cells in a biological sample, may be assembled together in a kit. This will generally comprise of the preselected primers for two, or more, particular specific markers. Also included may be enzymes suitable for amplifying nucleic acids including various polymerases (RT, Taq, etc.), deoxynucleotides and buffers to provide the necessary reaction mixture for amplification.

Such kits will generally comprise, in suitable means, distinct containers for each individual reagent and enzyme as well as for each marker primer pair. In one embodiment, the kit comprises primers for amplifying nucleic acids targets from a panel of marker genes, wherein the panel comprises GalNAcT, PAX3, or both, and containers for each of the pairs of primers. In another embodiment, the kit further comprises primers from marker genes selected from a group consisting of MAGE-A3, MART-1, MITF, TRP-2, and Tyrosinase.

Kits of the present invention, also will typically include a means for containing the reagents in close confinement for commercial sale such as, e.g., injection or blow-molded plastic containers into which the desired reagent are retained. Other containers suitable for conducting certain steps of the disclosed methods also may be provided.

The foregoing is meant to illustrate, but not to limit, the scope of the invention. Indeed, those of ordinary skill in the art can readily envision and produce further embodiments, based on the teachings herein, without undue experimentation.

Example 1

Patients and Tumors

SLN specimens were obtained in consultation with the surgeon and pathologist at the John Wayne Cancer Institute (JWCI). Informed human subject IRB consent was obtained from patients for the use of all specimens. All patients had AJCC stage I or II malignant melanoma (staged by current AJCC staging system) (Balch, C. M., 2001) which are defined as those patients with no clinical evidence of regional or metastatic disease. SLND was performed in the patients as previously described (Morton, D. L., 1992). Total 308 SNs obtained from 215 patients were assessed for histopathologic examination and qRT-PCR assay. The patients ranged in age from 18.7 to 91.3 years old (mean age 50.9±15.9 SD), consisting of 127 males and 88 females. The patients who had histopathologically (H&E/IHC) proven metastatic melanoma in SLNs at SLND subsequently received complete lymph node dissection of the lymphatic basin. Patients were followed up by clinical diagnostic examinations in the outpatient clinic. The patients who had melanoma recurrence after SLND received a variety of adjuvant therapies (immunotherapy, chemotherapy, or biochemotherapy) (Morton, D. L., 1992; Morton, D. L., 1996; O'Day, S. J., 2002). The personnel performing the qRT-PCR assay did not know the disease outcome of patients. The JWCI melanoma computer database analysis with patients' follow-up and history was independently provided to a biostatistician.

Thirty-two pathology-verified metastatic lesions from melanoma patients undergoing elective surgeries at JWCI were used for positive controls and for assessing receiver operating characteristic (ROC) curves (Henderson, A. R., 1993; Mitas, M., 2001). After the patients provided informed consent, 39 pathology-defined cancer negative lymph nodes obtained from patients undergoing tonsilectomy, colorectomy or breast surgery were utilized as negative controls and for assessing ROC curves.

Ten melanoma cell lines (MA, MB, MC, MD, ME, MF, MG, MH, MI, and MJ) established and characterized at the John Wayne Cancer Institute (JWCI) were used as positive controls for the qRT-PCR assay. All established cell lines were grown in RPMI-1640 medium supplemented with 100 ml/L heat-inactivated fetal calf serum, penicillin, and streptomycin (GIBCO, Grand Island, N.Y.) in T75-cm$^2$ flask as described previously (Miyashiro, I., 2001). Total RNA was extracted from cells when cell cultures reached 70-80% confluence.

Example 2

Histopathologic Examination and RNA Isolation

Histopathologic examination by the pathologists was performed on each collected SN as previously described (Bostick, P. J., 1999, which is incorporated herin by the reference). Each SN was bisected, and an 8-μm imprint slide was then prepared from the tissue surface and stained with Diff-Quik I & II (Dade International, Miami, Fla.) for the pathologist's intraoperative diagnosis. If melanoma cells were identified in the frozen section, a complete lymph node dissection was then performed (Bostick, P. J., 1999). Six immediately adjacent frozen sections were cut on the cryostat to a thickness of 12 μm each and stored at −80° C. until processed at a later date (Bostick, P. J., 1999; Miyashiro, I., 2001). The remainder of the bisected node, which was not frozen, was then placed in 10% formalin and embedded in paraffin, and 4-μm-thick sections were examined with H&E staining. Adjacent 4-μm-thick sections werre evaluated by IHC using antibodies to HMB-45 and S-100 proteins. This PE section evaluation was performed at two different levels separated by approximately 40 μm.

For qRT-PCR assay, additional 10 sections of 10-μm thick tissues were cut from each tissue specimen embedded in paraffin using a microtome and new sterile blade. The sections were placed in a sterile container for deparaffinization with xylene. Deparaffinized tissue sections were then subjected to proteinase K digestion and RNA extraction using the Paraffin Block RNA Isolation Kit (Ambion, Austin, Tex.). Briefly, tissues were digested, RNA was solubilized in a guanidinium-based buffer, the separation of RNA was achieved by using phenol:chloroform, and isopropanol was used to precipitate the RNA. Pellet Paint (Novagen, Madison, Wis.) was also used in the precipitation procedure to enhance the recovery of RNA. The RNA was dissolved in molecular grade water and quantified using a spectrophotometer and RIBOGreen detection assay (Molecular Probes, OR). Total cellular RNA from cell lines and frozen tissue specimens was extracted, isolated and purified using Tri-Reagent (Molecular Research Center, Cincinnati, Ohio) as previously described (Sarantou, T., 1997; Bilchik, A. J., 2001). All RNA extractions were performed in a designated sterile laminar flow hood using RNAse-free lab ware. Tissue processing, RNA extraction, RT-PCR assay set-up, and post-RT-PCR product analysis were performed in separate designated rooms to prevent cross-contamination, as previously reported (Bostick, P. J., 1999).

Example 3

Dilution Study

To verify the specificity of detecting occult metastasis, total RNA was extracted from 1000 melanoma cells of obviously metastatic melanoma tissue (n=8) in PE sections using laser capture microdissection (LCM). Five-μm thick sections were cut from each tissue specimen embedded in paraffin using a microtomb and mounted on a slide. Then, tissue sections were deparaffinized with xylene and subsequently stained with H&E. After drying a slide, 1000 metastatic melanoma cells were microdissected using the PixCell II LCM System (Arcturus Engineering, Mountain View, Calif.) as manufacture's procedure. Microdissected tissues were digested with proteinase K and total RNA was extracted using the Paraffin Block RNA Isolation Kit (Ambion). RNA isolated from 1000 melanoma cells was dissolved in molecular grade water, and was serially diluted by ½, ¹/₁₀, ¹/₂₀, ¹/₅₀, ¹/₁₀₀, ¹/₅₀₀, and ¹/₁₀₀₀. Reverse transcriptase reaction and qRT-PCR assays were performed for each marker on the diluted RNAs.

Example 4

Primers and Probes

Primer and probe sequences were designed for the Real-Time PCR assay using Oligo Primer Analysis Software, version 5.0 (National Biomedical systems, Plymouth, Minn.). To avoid possible amplification of contaminating genomic DNA, primers were designed so that each PCR product covered at least one intron. Fluorescence Resonance Energy Transfer (FRET) probe sequences were as follows:

```
MART-1:
                                          (SEQ ID NO: 1)
5'-FAM-CAG AAC AGT CAC CAC CAC CTT ATT-BHQ-1-3';

MAGE-A3:
                                          (SEQ ID NO: 2)
5'-FAM-AGC TCC TGC CCA CAC TCC CGC CTG T-BHQ-1-3';

GalNAcT:
                                          (SEQ ID NO: 3)
5'-CAL RED-ATG AGG CTG CTT TCA CTA TCC GCA-BHQ-2-
3';

PAX3,
                                          (SEQ ID NO: 4)
5'-FAM-CCA GAC TGA TTA CGC GCT CTC CC-BHQ-1-3';

Glyceraldehydes-3-phosphate dehydrogenase (GAPDH):
                                          (SEQ ID NO: 5)
5'-FAM-CAG CAA TGC CTC CTG CAC CAC CAA-BHQ-1-3'.
```

Control melanomas and non-melanoma tissues and cell lines were used to optimize the assay. GAPDH was utilized as internal reference house-keeping genes for status of sample mRNA assessed.

Additionally, the following probes may be used:

```
MITF:
                                          (SEQ ID NO: 6)
5'-FAM-AGA GCA CTG GCC AAA GAG AGG CA-BHQ-1-3'.

TRP-2:
                                          (SEQ ID NO: 7)
5'-FAM-TCA CAT CAA GGA CCT GCA TTT GTT A-BHQ-1-3'.

Tyrosinase (TYR):
                                          (SEQ ID NO: 8)
5'-FAM-TTC ACC ATG CAT TTG TTG ACA GTA TT-BHQ-1-3'.

C-MET:
                                          (SEQ ID NO: 9)
5'-FAM-TGG GAG CTG ATG ACA AGA GGA G-BHQ-1-3'.

Stanniocalcin-1:
                                          (SEQ ID NO: 10)
5'-FAM-CCT GCT GGA ATG TGA TGA AGA CAC-BHQ-1-3'.

Mammoglobin:
                                          (SEQ ID NO: 11)
Sense: 5'-CACTGCTACGCAGGCTCT -3';

(SEQ ID NO: 12)
Antisense: 5'-TGCTCAGAGTTTCATCCG -3'.

HSP27:
                                          (SEQ ID NO: 13)
5'-FAM-AGG AGC GGC AGG ACG AGC AT-BHQ-1-3'.
```

-continued

Cytokeratin 20:
(SEQ ID NO: 14)
5'-FAM-ATC AGT TAA GCA CCC TGG AAG AGA G-BHQ-1-3'.

Beta-HCG:
(SEQ ID NO: 15)
5'-FAM-CCT GCC TCA GGT GGT GTG CAA C-BHQ-1-3'.

The above-listed probes are examples of probes that may be used. Those skilled in the art will recognize that the sequences of markers of the present invention are known and other primers for the markers of the present invention can be easily synthesized.

Example 5 qRT-PCR Assay

All reverse transcriptase reactions were performed using Moloney murine leukemia virus reverse transcriptase (Promega, Madison, Wis.) with both oligo-dT (Gene Link, Hawthorne, N.Y.) and random hexamers (Roche) priming for a more complete transcription of all RNA including the fragmented RNA often found in paraffin-embedded specimens as previously described (Bostick, P. J., 1999; Miyashiro, I., 2001). The RealTime PCR assay was performed using iCycler iQ RealTime Thermocycler (4 color) Detection System (Bio-Rad Laboratories, Hercules, Calif.). The PCR reaction mixture consisted of cDNA template from 250 ng of total RNA, 1 µM of each primer, 0.3 µM FRET probe, 1 U AmpliTaq Gold polymerase (Applied Biosystems, Branchburg, N.J.), 200 µM of each dNTP, 4.5 mM MgCl2, 10 µg of bovine serum albumin, and 10× AmpliTaq Buffer to a final volume of 25 µl. Samples were amplified with a precycling hold at 95° C. for 10 min, followed by 45 cycles of denaturation at 95° C. for 1 min, annealing at 55° C. for 1 min for GAPDH, annealing at 58° C. for MAGE-A3 (40 cycles), at 62° C. for MART-1, at 62° C. for GalNAc-T (42 cycles), at 65° C. for Pax3, and extension at 72° C. for 1 min. The following conditions may be used for other markers: 59° C. for MITF; 62° C. for TRP-2 (42 cycles); 58° C. for tyrosinase; 55° C. for C-MET; 54° C. for stanniocalcin-1; 59° C. for HSP 27; 55° C. for cytokeratin 20; and 60° C. for beta-HCG.

For ROC curve analysis, all reactions were performed at same conditions but 45 cycles. All PCR conditions and annealing temperature for each marker were optimized at initial experiments and ROC curve analysis.

Positive controls (melanoma cell lines and PE metastatic melanoma tissues), negative controls from tumor-free lymph nodes, and reagent controls (reagent alone without RNA or cDNA) for the qRT-PCR assays were included in each assay run. Each assay was performed at least three times to verify the results and the mean copy number was used for analysis. If twice or more positive copy numbers were obtained in the same sample, the sample by the marker was considered to be positive. If only once positive copy number was detected in the three assays, the sample was thought to be negative. In the patient who have two or more identified SLNs, the highest copy number among them was listed as a chosen value.

The standard curve for quantifying mRNA copy number was established by amplifying nine aliquots of templates with known copy numbers ($10^0$ to $10^8$ copies). Specific MAA cDNA was synthesized as follows; RT-PCR and sample RNA was performed, run on 2% agarose gel electrophoresis, and the cDNA was extracted using the QIAquick gel extraction method (Qiagen, Valencia, Calif.) according to the manufacturer's instructions. The MAA cDNA was ligated into pCR II-TOPO cloning vector (Invitrogen, San Diego, Calif.), the cDNA clones were transformed into *Escherichia coli* DH5-α cells, and cultures were expanded as previously described (Miyashiro, I., 2001). Plasmids containing the target gene were purified and quantified for use in the RealTime PCR setup. To confirm that the inserted PCR product size is correct, plasmids were digested with specific restriction enzymes, and the cDNA clone PCR products were then run on gel electrophoresis.

Example 6

Statistical Analysis

To investigate the association between single and multimarker combinations and clinicopathological parameters, Student's t-test was used for continuous variables. Chi-square test was used for categorical variables. Kappa analysis and Spearman correlation coefficient analysis were used for the comparison between the copy numbers of each mRNA marker. The cumulative disease-free survival rates for patient groups were calculated using the Kaplan-Meier methods and compared by using the log-rank test. Cox proportional hazard model was used for multivariate analysis of variables associated with the disease-free survival. All p values which were two-sided at a value of $\leq 0.05$ were considered to be statistically significant.

Example 7

MAA Expression in Melanoma Cell Lines

Figure 1B:
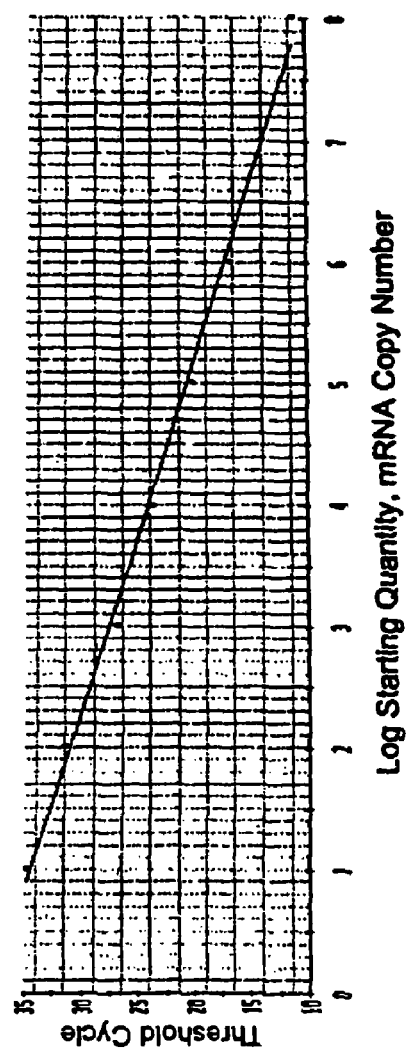
FIG. 1B shows the standard curve (correlation coefficient 0.998) generated by using the threshold cycle (Ct) of templates with known numbers of copies. Symbol o indicates standards.

MART-1, MAGE-A3, GalNAc-T, and PAX3 mRNA expressions were measured by qRT-PCR assay in ten melanoma cell lines. The PCR amplification of the serially diluted cDNA standard templates of each marker showed a logarithmic signal increase (FIG. 1A, representative qRT-PCR analysis for MART-1). The standard curve was generated by using the threshold cycle (Ct) of templates with known numbers of copies (FIG. 1B, only for MART-1 is shown). The Ct of each sample was plotted on the standard curve, and the mRNA copy number was calculated by the iCycler iQ RealTime Detection System Software (Bio-Rad Laboratories). All four markers were expressed in every melanoma cell line.

The MART-1 mRNA copy number ranged from $5.66 \times 10^3$ to $4.56 \times 10^7$ copies (median $2.32 \times 10^7$ copies) per 250 ng of total RNA from 10 individual melanoma cell lines. The MAGE-A3 mRNA copy number ranged from $6.34 \times 10^3$ to $1.31 \times 10^6$ copies (median $7.61 \times 10^5$ copies), the GalNAc-T mRNA copy number ranged from 24 to $5.05 \times 10^5$ copies (median $3.58 \times 10^4$ copies), and the PAX3 mRNA copy levels were from $2.25 \times 10^4$ to $4.00 \times 10^5$ copies (median $2.12 \times 10^5$ copies). The house-keeping gene GAPDH mRNA copy number ranged from $3.19 \times 10^7$ to $1.56 \times 10^8$ copies (median $1.05 \times 10^8$ copies). The marker expressions and the size of PCR products were certified by a run on 2% agarose gel electrophoresis after qRT-PCR assay.

Example 8

ROC Curves Analysis

Figure 2:
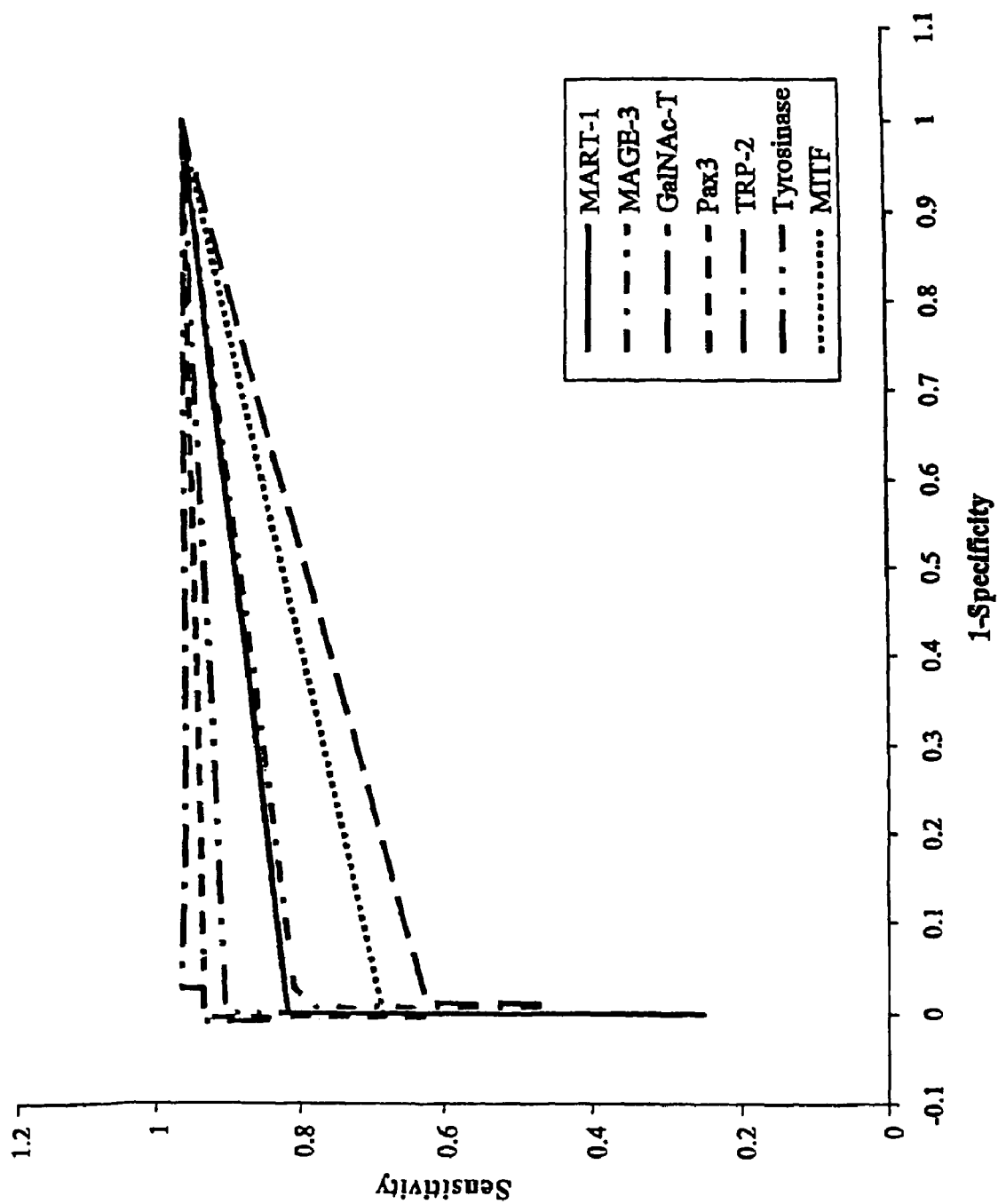
FIG. 2 provide receiver operating characteristic (ROC) curves for mRNA tumor markers.

ROC curve analysis was performed to define the diagnostic accuracy of the MM qRT-PCR assay of the present invention for the detection of metastatic melanoma in PE specimens. Each marker mRNA copy level in 32 pathology-verified metastatic lesions from melanoma patients was significantly higher than that in 39 pathology-defined cancer negative lymph nodes. ROC curve analysis is based on a plot of sensitivity as a function of 1-specificity (Henderson, A. R., 1993; Mitas, M., 2001). FIG. 2 provides ROC curves for various markers.

TABLE 1

ROC curves analysis

| Marker | W (Area under ROC curve) ± SE | Sensitivity | Specificity |
|---|---|---|---|
| MART-1 | 0.906 ± 0.039 | 0.813 | 1.000 |
| MAGE-A3 | 0.903 ± 0.039 | 0.781 | 1.000 |
| GalNAcT | 0.813 ± 0.053 | 0.594 | 1.000 |
| PAX3 | 0.968 ± 0.023 | 0.969 | 0.923 |

ROC curve analysis is the most commonly used statistical method for assessing the accuracy of diagnostic tests (Henderson, A. R., 1993; Mitas, M., 2001). The area under the ROC curve with a defined confidence interval is a measure of diagnostic accuracy such that values between 0.5 and 0.7 indicate low accuracy, values between 0.7 and 0.9 indicate moderate accuracy and values more than 0.9 indicate high accuracy.

In this study, the value of each marker was as follows; MART-1, W=0.906; MAGE-A3, 0.903; GalNAc-T, 0.813; PAX3, 0.968 (Table 1 and FIG. 2). The sensitivity and specificity for given cut-off points (optimized PCR cycle number) were also evaluated (Table 1). None of the MART-1, GalNAcT and MAGE-A3 mRNA copy levels were expressed under the assay's optimal conditions in normal lymph nodes (n=39). Thus, the methods of the present invention, unlike conventional methods do not produce false-positive results. Only one normal lymph node expressed PAX3 mRNA, however, the copy number was one. The values in ROC curve analysis and the sensitivity and specificity of each marker were acceptable and feasible for detection of metastatic melanoma in PE specimens.

Example 9

Comparison Between Frozen and PE Specimens in the SLN Sample

The sensitivity of the MM qRT-PCR assay was further validated by comparing for each marker mRNA copy level of paraffin-embedded specimens with frozen sections in 31 SLNs (ten SLNs were pathology defined melanoma-positive lymph nodes, and 21 SLNs were histologically negative).

TABLE 2

Consistency of mRNA expression between paraffin-embedded and frozen SLNs

| | | Kappa analysis | | | Spearman correlation coefficient | |
|---|---|---|---|---|---|---|
| Marker | Consistency of results (%) | Coefficient | 95% CI | p-value | Coefficient | p-value |
| MART-1 | 30/31 (97%) | 0.912 | 0.744, 1.081 | <0.0001 | 0.963 | <0.0001 |
| MAGE-A3 | 27/31 (87%) | 0.597 | 0.260, 0.934 | 0.0022 | 0.868 | <0.0001 |
| GalNAc-T | 27/31 (87%) | 0.688 | 0.409, 0.968 | 0.0003 | 0.835 | <0.0001 |
| PAX3 | 30/31 (97%) | 0.912 | 0.744, 1.081 | <0.0001 | 0.970 | <0.0001 |

Positivity of each marker in PE sections was highly coincided with that in corresponding frozen sections (Table 2). Moreover, Spearman correlation coefficient analysis and Kappa analysis revealed significant correlation in each marker mRNA copy level between PE sections and corresponding frozen sections (Table 2). Surprisingly, the study demonstrated not only a high coincidence of positivity but also significant correlation in each marker mRNA copy level between frozen and PE specimens. The study revealed that marker panels of the present invention can be used in both PE and frozen specimens.

Example 10

Dilution Study

The sensitivity of mRNA marker detection by the qRT-PCR assay was verified by serial dilution analysis of total RNA from 1000 melanoma cells obtained from paraffin-embedded specimens using the LCM. The assays were repeated at least three times for each marker to verify the results and reduce false-positive and false-negative results. Representative results are shown as Table 3.

In several samples, MART-1, MAGE-A3, GalNAcT and PAX3 mRNA copy levels were detectable in 1/100 diluted total RNA which is approximately equal to total RNA from 10 melanoma cells in the qRT-PCR assay.

Dilution study using the LCM was performed to define the sensitivity for detection of PE occult melanoma cells in the assays. It is known that the mRNA levels for individual markers vary in individual melanoma cells because inter- and intra-tumor heterogeneity. Therefore the results may not always representative of all SLN specimens assessed in this study. However, the detection sensitivities obtained in the present invention (10 to 50 metastatic melanoma cells in 100-mm thick PE SLN) unexpectedly allow detection of occult melanoma cells in SLNs.

TABLE 3

| | | Copy number at the diluted samples (No. of estimated melanoma cells) | | | | | | |
|---|---|---|---|---|---|---|---|---|
| Marker | Sample | 1 (1000) | 1/2 (500) | 1/10 (100) | 1/20 (50) | 1/100 (10) | 1/200 (5) | 1/1000 (1) |
| MART-1 | A | 167 | 139 | 38 | 7 | 2 | 0 | 0 |
| | B | 39 | 31 | 3 | 2 | 0 | 0 | 0 |
| | C | 166 | 83 | 12 | 2 | 0 | 0 | 0 |
| MAGE-A3 | B | 183 | 161 | 8 | 2 | 1 | 0 | 0 |
| | C | 243 | 157 | 31 | 6 | 1 | 0 | 0 |
| | D | 70 | 35 | 5 | 2 | 0 | 0 | 0 |
| GalNAc-T | E | 18 | 12 | 4 | 2 | 0 | 0 | 0 |
| | F | 19 | 8 | 6 | 2 | 1 | 0 | 0 |
| | G | 7 | 4 | 1 | 0 | 0 | 0 | 0 |

TABLE 3-continued

| Marker | Sample | \multicolumn{7}{c}{Copy number at the diluted samples (No. of estimated melanoma cells)} |
|---|---|---|---|---|---|---|---|---|
| | | 1 (1000) | 1/2 (500) | 1/10 (100) | 1/20 (50) | 1/100 (10) | 1/200 (5) | 1/1000 (1) |
| pax3 | A | 47 | 18 | 2 | 1 | 0 | 0 | 0 |
| | C | 74 | 33 | 5 | 3 | 1 | 0 | 0 |
| | D | 42 | 22 | 12 | 0 | 0 | 0 | 0 |

Example 11

MM qRT-PCR Assay in PE SLNs

MART-1, MAGE-A3, GalNAcT, and PAX3 mRNA copy levels were assessed using the qRT-PCR assay on 308 SLNs obtained from 215 clinically early-stage melanoma patients who underwent SLND. Of the 53 patients with histopathologically proven melanoma cells (48 detected by H&E staining, seven by IHC alone) in the SLN, MART-1, MAGE-A3, GalNAcT, and PAX3 mRNA markers were expressed in the SLNs of 38 (72%), 24 (45%), 34 (64%), and 37 (70%) patients, respectively (Table 4). Among the patients with histopathologically positive SLNs, 47 (89%) of 53 expressed at least one detectable mRNA marker, and 20 patients (38%) demonstrated all four marker mRNA expression (Table 4). On the other hand, MART-1, MAGE-A3, GalNAcT, and PAX3 marker expression were detected from 162 patients with histopathologically proven melanoma-free SLNs (no evidence of tumor cells in SLN by H&E staining or IHC) as follows: 10 (6%), 8 (5%), 27 (17%), 28 (17%), respectively. Positivity of each mRNA marker in histopathologically positive SLNs was significantly higher than that in histopathologically negative SLNs (Table 4). Among 162 patients with histopathologically negative SLNs forty-eight patients (30%) had at least one melanoma marker detected and 19 patients (12%) had two or three markers expressed. No patients with histopathologically negative SLNs demonstrated all four marker expression.

Each mRNA copy number per 250 ng of total RNA in SLN from 215 patients ranged as follows: MART-1, 0 to 547,400 mRNA copies (mean±SD: 5,926±45,876 copies); MAGE-A3, 0 to 1,980 copies (28±160 copies); GalNAc-T, 0 to 13,710 copies (88±938 copies); Pax3, 0 to 11,060 copies (190±917 copies). Mean copy level for each mRNA marker in histopathologically positive SLNs was significantly higher than that in histopathologically negative SLNs (Table 4). Patients' age, Breslow's thickness, and Clark level were also significantly different between histopathologically positive and negative SLN patients, respectively (Table 4). The study may suggest that mRNA marker copy labels by the qRT-PCR assays of the present invention are generally reflected by tumor volume or number of melanoma cells in SLN in spite of the tumor heterogeneity.

Spearman correlation coefficient analysis also showed a significant correlation (p<0.001) in comparison of MART-1 vs. MAGE-A3, MART-1 vs. GalNAcT, MART-1 vs. PAX3, MAGE-A3 vs. GalNAcT, MAGE-A3 vs. PAX3, and GalNAcT vs. PAX3 with the correlation coefficient 0.560, 0.488, 0.514, 0.526, 0.506, and 0.465, respectively. All SLN specimens were positive for GAPDH showing high integrity of the mRNA extracted from the tumor specimens. The GAPDH mRNA copy number ranged from $1.02 \times 10^3$ to $7.24 \times 10^6$ copies (median $3.24 \times 10^4$ copies).

TABLE 4

Correlation of mRNA Markers with Histopathology Status of the SLNs

| Risk Factor | H&E/IHC(+) SLN (n = 53) | H&E/IHC(−) SLN (n = 162) | p value |
|---|---|---|---|
| Age (mean +/− SD) | 46.5 | 52.3 | 0.02 |
| Gender: | | | |
| Male | 30 | 97 | |
| Female | 23 | 65 | 0.8 |
| Primary Site | | | |
| Head/neck | 5 | 26 | |
| Trunk | 20 | 66 | |
| Extremity | 28 | 70 | 0.35 |
| Breslow thickness (mm) | | | |
| <=1.00 | 6 | 55 | |
| 1.01-2.00 | 20 | 65 | |
| 2.01-4.00 | 19 | 26 | |
| >4.00 | 7 | 13 | 0.001 |
| Mean +/− SD(mm) | 2.86 +/− 2.6 | 1.9 +/− 1.8 | 0.003 |
| Clark level | | | |
| 1 | 0 | 2 | |
| 2 | 4 | 11 | |
| 3 | 10 | 65 | |
| 4 | 35 | 72 | |
| 5 | 3 | 8 | 0.03 |
| MART-1 expression | | | |
| Positive | 15 | 152 | |
| Negative | 38 | 10 | <0.0001 |
| MART-1 copy number | | | |
| (Mean +/− SD) | 24029 +/− 90652 | 3.4 +/− 27 | 0.0008 |
| GalNAc-T expression | | | |
| Positive | 19 | 135 | |
| Negative | 34 | 27 | <0.0001 |
| GalNac-T copy number | | | |
| (Mean +/− SD) | 331 +/− 1882 | 7.9 +/− 29 | 0.03 |
| Pax3 expression | | | |
| Positive | 16 | 134 | |
| Negative | 37 | 28 | <0.0001 |
| Pax3 copy number | | | |
| (Mean +/− SD) | 701 +/− 1734 | 22.7 +/− 177 | <0.0001 |
| MAGE-A3 expression | | | |
| Positive | 29 | 154 | |
| Negative | 24 | 8 | <0.0001 |
| MAGE-A3 copy number | | | |
| (Mean +/− SD) | 114 +/− 309 | 0.2 +/− 1 | <0.0001 |
| Number of mRNA marker | | | |
| 0 | 6 | 114 | |
| 1 | 9 | 29 | |
| 2 | 10 | 13 | |
| 3 | 8 | 6 | |
| 4 | 20 | 0 | <0.0001 |

Figure 3:
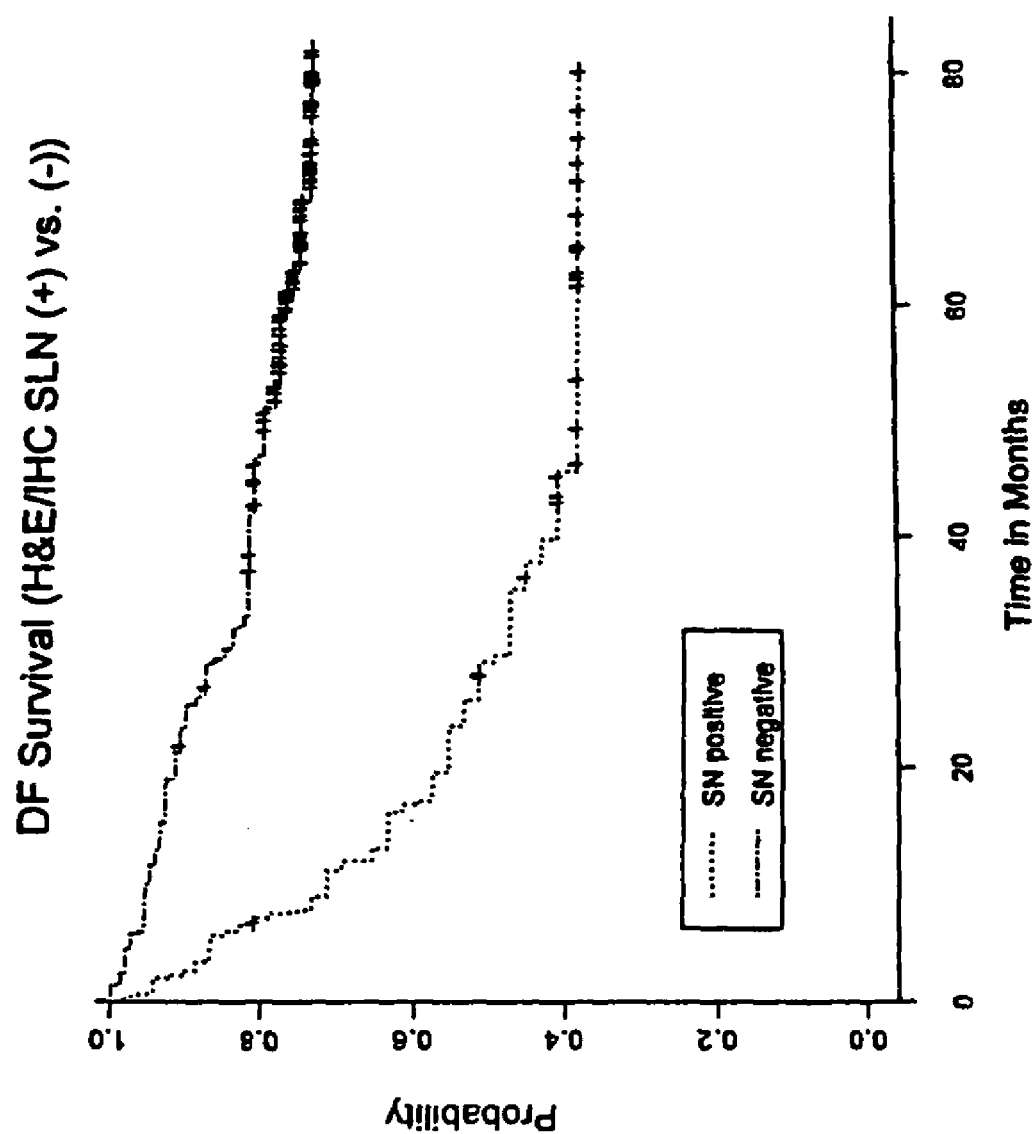
FIG. 3 shows the disease free survival (DFS) rate for patients with histopathologically positive and negative SLNs.
Figure 4A:
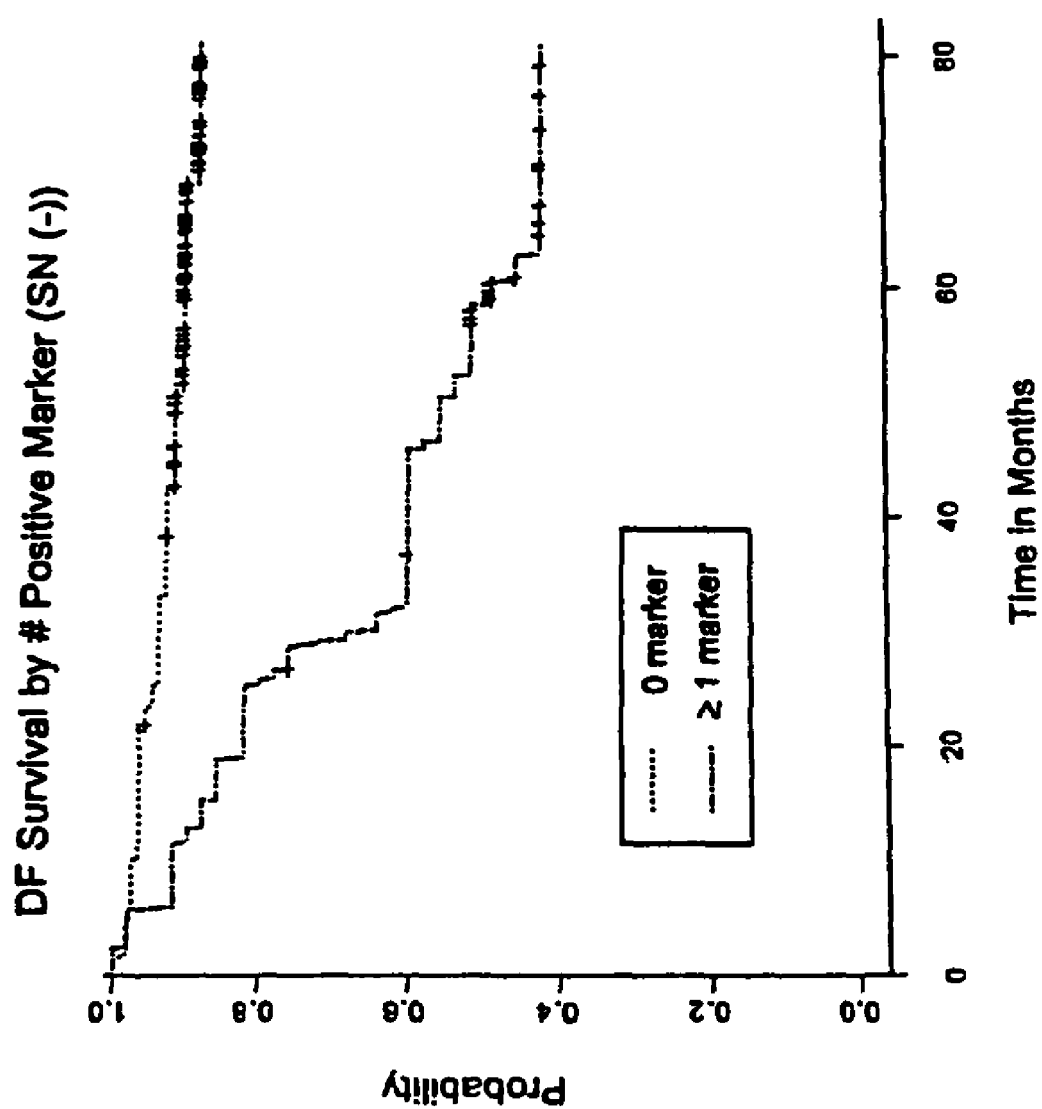
FIG. 4A shows DFS rate for melanoma patients with histopathologically negative SLNs with no mRNA markers expressed and with one or more mRNA markers expressed in accordance with one embodiment of the present invention, in which of MART-1, MAGE-A3, GalNAcT, and PAX3 markers were utilized.
Figure 4B:
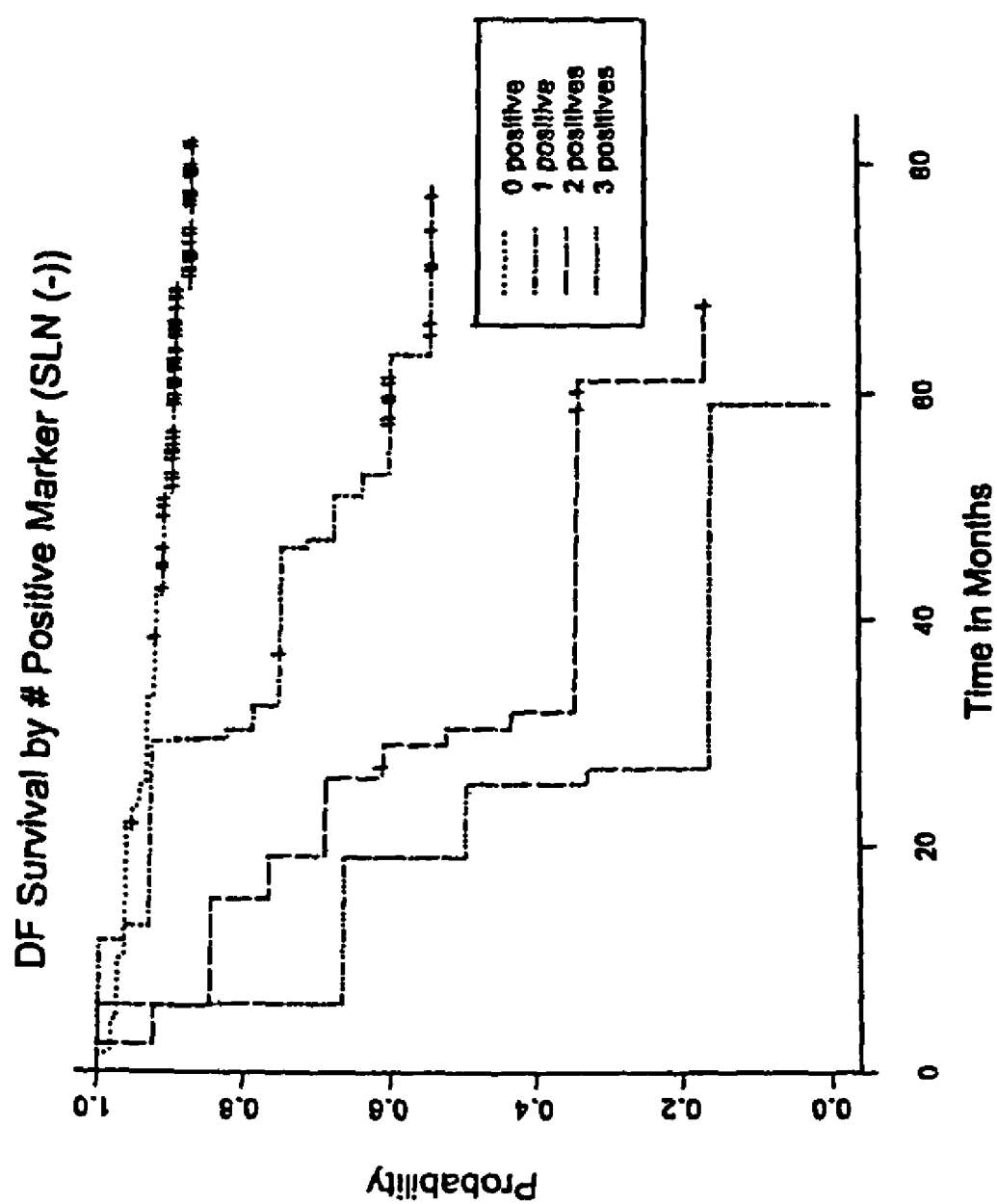
FIG. 4B shows DFS rate for melanoma patients with histopathologically negative SLNs with no mRNA markers expressed and with one, two or three mRNA markers expressed in accordance with one embodiment of the present invention, in which of MART-1, MAGE-A3, GalNAcT, and PAX3 markers were utilized.

In a median follow-up period of 60.4 months, thirty-one (58%) of 53 patients with histopathologically positive SLNs and 39 (24%) of 162 patients with histopathologically negative SLNs have recurred after SLND. The disease free survival (DFS) rate for 53 patients with histopathologically positive SLNs was significantly lower than for 162 patients with histopathologically negative SLNs (Log-rank test p<0.0001; FIG. 3, Table 4). Among the 162 patients with histopathologically negative SLNs, only 12 (11%) of the 114 patients with SLNs that were with histopathologically negative and had no mRNA marker expressed had recurrence of disease. Among the 48 patients with SLNs that were histopathologically negative SLNs but which expressed one or more mRNA markers, 56% (27 of 48) had recurrence. A significantly worse DFS was associated with patients whose histopathologically negative SLN expressed one or more mRNA markers as compared to those patients with no mRNA marker present (p<0.0001) (Table 5). In particular, the increased number of mRNA marker expression significantly correlated with worse DFS rate among histopathologically negative SLN patients (FIG. 4A). There have been 12 (41%) recurrences in 29 patients with one mRNA marker expressed, 10 (71%) recurrences in 14 patients with two markers expressed, and 5 (100%) recurrences in 5 patients with three marker expression (FIG. 4b).

By multivariate analysis using Cox proportional hazard model, histopathologically negative SLN patients at increased risk of recurence had the combination of the MM expression (RR 3.26, 95% CI: 2.4-4.4, p<0.0001) and Breslow's thickness (RR 1.21, 95% CI: 1.1-1.4, p=0.01). In histopathologically negative SLN patients, the mRNA copy number of each marker in patients who recurred was significantly higher than that in patients who did not recur (p<0.001; Table 6). Among the total 215 patients, only MAGE-A3 mRNA copy levels correlated with disease recurrence (mean copy number in the patients with recurrence vs. no recurrence; 64±265 vs 11±59; p=0.02).

TABLE 5

Prognostic Significance of mRNA Marker Detection in the SLN virsus Disease Recurrence

| Risk Factor | No recurrence (n = 123) | Recurrence (n = 39) | p value |
|---|---|---|---|
| Age (mean +/- SD) | 51.9 +/- 16.3 | 53.5 +/- 15 | 0.58 |
| Gender: | | | |
| Male | 72 | 25 | |
| Female | 51 | 14 | 0.53 |
| Primary Site | | | |
| Head/neck | 15 | 11 | |
| Trunk | 57 | 9 | |
| Extremity | 51 | 19 | 0.011 |
| Breslow thickness (mm) | | | |
| T1 <= 1.00 | 48 | 10 | |
| T2 1.01-2.00 | 52 | 13 | |
| T3 2.01-4.00 | 14 | 12 | |
| T4 <4.00 | 9 | 4 | 0.025 |
| Mean +/- SD(mm) | 1.7 +/- 1.6 | 2.4 +/- 2.0 | 0.034 |
| Clark level | | | |
| 1 | 2 | 0 | |
| 2 | 7 | 4 | |
| 3 | 54 | 11 | |
| 4 | 52 | 20 | |
| 5 | 6 | 2 | 0.41 |
| AJCC stage | | | |
| I (T1 and N0) | 48 | 10 | |
| II (T2 or T3 or T4 and N0) | 75 | 28 | |
| III (Any T and N1/2) | 0 | 0 | 0.13 |
| MART-1 expression | | | |
| Positive | 3 | 7 | |
| Negative | 120 | 32 | <0.0005 |
| MART-1 copy number | | | |
| (Mean +/- SD) | 44.8 +/- 309 | 16904 +/- 76801 | 0.01 |
| GalNAc-T expression | | | |
| Positive | 8 | 19 | |
| Negative | 115 | 20 | <0.0001 |
| GalNac-T copy number | | | |
| (Mean +/- SD) | 17 +/- 63 | 219 +/- 1585 | 0.13 |
| Pax3 expression | | | |
| Positive | 13 | 15 | |
| Negative | 110 | 24 | <0.00006 |
| Pax3 copy number | | | |
| (Mean +/- SD) | 61.7 +/- 384 | 429 +/- 1436 | <0.005 |
| MAGE-A3 expression | | | |
| Positive | 1 | 7 | |
| Negative | 122 | 32 | <0.00002 |
| MAGE-A3 copy number | | | |
| (Mean +/- SD) | 6.7 +/- 42 | 68.5 +/- 261 | <0.007 |
| Number of mRNA marker | | | |
| 0 | 102 | 12 | |
| 1 | 17 | 12 | |
| 2 | 4 | 9 | |
| 3 | 0 | 6 | |
| 4 | 0 | 0 | <0.0001 |

TABLE 6

Cox Proportional Hazards Model of Multi Marker RT-PCR

| | RR | Pvalue |
|---|---|---|
| Age (<60, >60) | 1.47 | 0.24 |
| Gender | 1.15 | 0.42 |
| Breslow | 1.15 | 0.037 |
| Clark | 1.57 | 0.0037 |
| Ulceration | 2.4 | 0.13 |
| Site (long rank test) | | 0.007 |
| Tyr | 6.7 | <0.001 |
| Mart | 10.1 | <0.001 |
| Trp | 5.57 | <0.001 |
| Galnac | 7.66 | <0.001 |
| Mitf | 6.03 | <0.001 |
| Pax3 | 4.66 | <0.001 |
| Mage | 7.21 | <0.001 |
| Total 1 (log rank test) | | <0.001 |
| Total 1 (0, 1, . . . , 7) | 1.8 | <0.001 |
| Total 2 (0, 1, 2+) | 4.46 | <0.001 |
| Total 3 (0-1, 2+) | 15.7 | <0.001 |

Table 6 gives the results of the univariate CoxPH analyses in the SN negative group. The markers are dichotomized as +/−expression. Total 1 is the number of positive markers. Total 2 uses two categories 0 positives, 1 positive or 2+ positive markers. Total 3 compares 0-1 positive markers vs 2+ positive markers. Two factors, site and total 1 employ the log rank test meaning that the variable was treated as a factor and we cannot compute an associated relative risk (RR).

Figure 5:
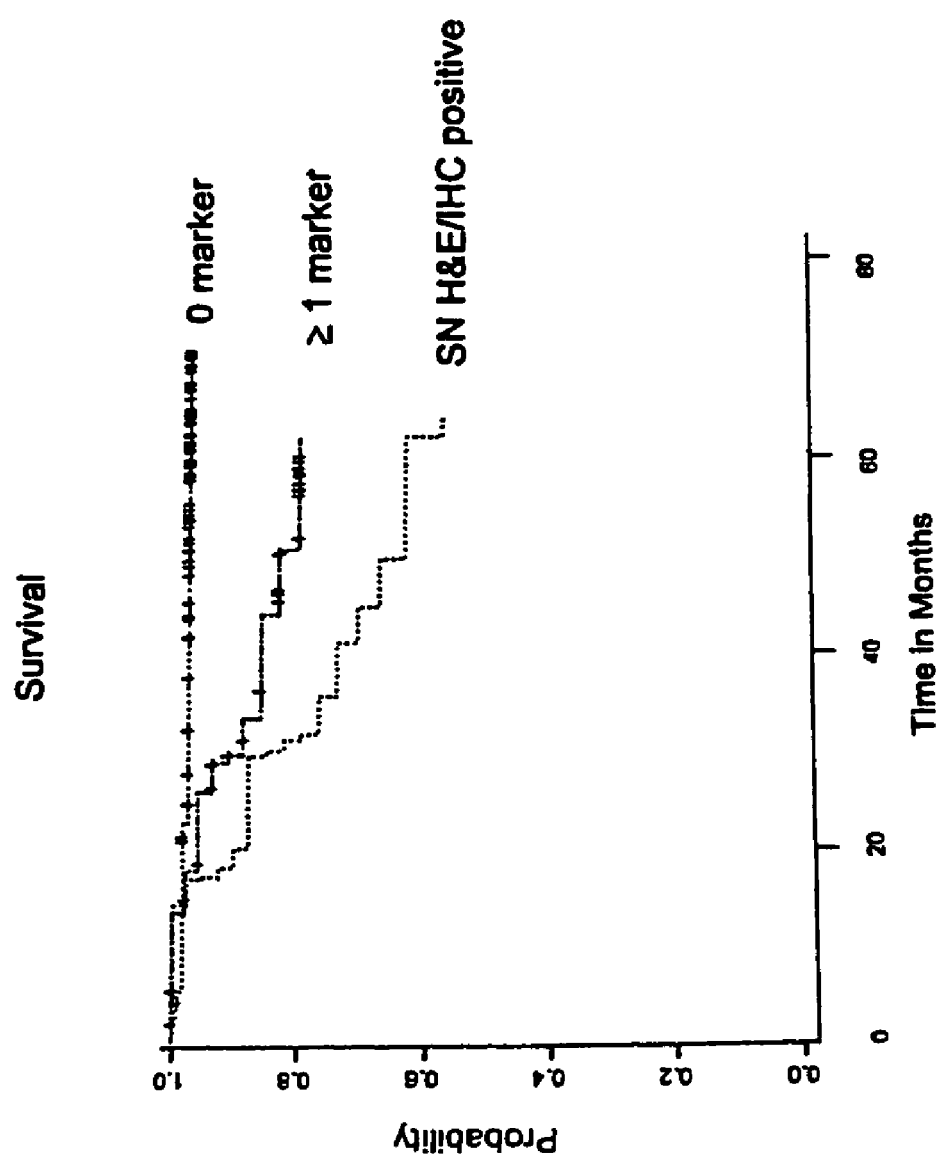
FIG. 5 shows DFS rate in accordance with one embodiment of the present invention, in which of MART-1, MAGE-A3, GalNAcT, and PAX3 markers were utilized. The graph shows DFS rate for patients with histopathologically negative SLNs; DFS for patients with no mRNA markers expressed; and DFS for patients with one or more mRNA expressed.

The correlation of MM expression by qRT-PCR with patient's survival was also assessed. The survival rate for 53 patients with histopathologically positive SLNs was significantly lower than for 162 patients with histopathologically negative SLNs (p<0.0001). Among the 162 patients with histopathologically negative SLNs, the survival rate for patients with one or more mRNA marker expression was significantly lower than that for patients with no mRNA marker expression (p<0.0001; FIG. 5). Furthermore the patient's worse survival correlated with the increased number of mRNA marker expression similar to the results of DFS analysis (p<0.0001).

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

REFERENCES

The following references, to the extent that they provide exemplary procedural or other details supplementary to those set forth herein, are specifically incorporated herein by reference.

1. Balch, C. M., Soong, S. J., Milton, G. W., Shaw, H. M., McGovern, V. J., Murad, T. M., et al. A comparison of prognostic factors and surgical results in 1,786 patients with localized (stage I) melanoma treated in Alabama, USA and New South Wales, Australia. Ann. Surg. 196:677-684, 1982.
2. Balch C M, Soong S J, Bartolucci A A, Urist M M, Karakousis C P, Smith T J, et al. Efficacy of an elective regional lymph node dissection of 1 to 4 mm thick melanomas for patients 60 years of age and younger. Ann Surg 1996; 224:255-63.
3. Balch, C. M., Buzaid, A. C., Soong, S-J., Atkins, M. B., Cascinelli, N., Coit, D. G., Fleming, I. D., Gershenwald, J. E., Houghton, A. Jr., Kirkwood, J. M., McMasters, K. M., Mihm, M. F., Morton, D. L., Reintgen, D. S., Ross, M. I., Sober, A., Thompson, J. A., and Thompson, J. F. Final version of the American Joint Committee on cancer staging system for cutaneous melanoma. J. Clin. Oncol. 16: 3635-3648, 2001.
4. Bilchik, A. J., Saha, S., Wiese, D., Stonecypher, J. A., Wood, T. F., Sostrin, S., Turner, R. R., Wang, H-J., Morton D. L., and Hoon, D. S. B Molecular staging of early colon cancer on the basis of sentinel node analysis: A multicenter phase II trial. J. Clin. Oncol, 19: 1128-1136, 2001.
5. Bostick, P. J., Morton, D. L., Turner, R. R., Huynh K. T., Wang, H-J., Elashoff R., Essner R., and Hoon, D. S. B Prognostic significance of occult metastases detected by sentinel lymphadenectomy and reverse transcriptase-polymerase chain reaction in early-stage melanoma patients. J. Clin. Oncol, 17: 3238-3244, 1999.
6. Cascinelli N, Morabito A, Santinami M, MacKie R M, Belli F. Immediate or delayed dissection of regional nodes in patients with melanoma of the trunk: a randomized trial. WHO Melanoma Programme. Lancet 1998; 351:793-6.
7. Clegg, R. M. Fluorescence energy transfer. Curr. Opin. Biotech., 6: 103-110, 1995.
8. Cochran A J, Wen D R, Herschman H R, et al. Occult melanoma in lymph nodes detected by antiserum to S-100 protein. Int J Cancer 1984; 34:159-63.
9. Final version of the American Joint Committee on cancer staging system for cutaneous melanoma. J. Clin. Oncol. 16: 3635-3648, 2001.
10. Goding C R. Mitf from neural crest to melanoma: signal transduction and transcription in the melanocyte lineage. Genes Dev 2000; 14:1712-28.
11. Henderson A R. Assessing test accuracy and its clinical consequences: a primer for receiver operating characteristic curve analysis. Ann Clin Biochem 1993; 30:521-29.
12. Hoon D S, Wang Y, Dale P S, Conrad A J, Schmid P, Garrison D, Kuo C K, Foshag L J, Nizze J A., Morton D L. Detection of occult melanoma cells in blood with a multiple-marker polymerase chain reaction assay. J. Clin. Oncol., 13: 2109-16, 1995.
13. Hoon D S, Banez M, Okun E, Morton D L, Irie R F. Modulation of human melanoma cells by interleukin-4 and in combination with γ-interferon or α-tumor necrosis factor. Cancer Res 1991; 51:2002-8.
14. Hoon D. S. B, Bostick P., Kuo, C., Okamoto T, Wang H-J., Elashoff, R., and Morton, D. L. Molecular markers in blood as surrogate prognostic indicators of melanoma recurrence. Cancer Res., 60: 2253-2257, 2000.
15. Jemal, A. J., Thomas, A., Murray, T., and Thun, M. Cancer Statistics, 2002. CA Cancer J. Clin., 52: 23-47, 2002.
16. Kawakami, Y., Eliyahu, S., Delgado, C. H., Robbins, P. F., Rivoltini, L., Topalian, S. L., Miki, T., and Rosenberg, S. A. Cloning of the gene coding for a shared human melanoma antigen recognized by autologous T cells infiltrating into tumor. Proc. Natl. Acad. Sci. USA, 91: 3515-3519, 1994.
17. Kawakami, Y., Eliyahu, S., Delgado, C. H., Robbins, P. F., Sakaguchi, K., Appella, E., Yannelli, J. R., Adema, G. J., Miki, T., and Rosenberg, S. A. Identification of a human melanoma antigen recognized by tumor-infiltrating lymphocytes associated with in vivo tumor rejection. Proc. Natl. Acad. Sci. USA, 91: 6458-6462, 1994.
18. Kuo C T, Bostick P J, Irie R F, Morton D L, Conrad A J, Hoon D S. Assessment of messenger RNA of β 1→4-N-acetylgalactosaminyl-transferase as a molecular marker for metastatic melanoma. Clin Cancer Res 1998; 4:411-8.
19. Li W, Stall A, Shivers S C, Lin J, Haddad F, Messina J, et al. Clinical relevance of molecular staging for melanoma: comparison of RT-PCR and immunohistochemistry staining in sentinel lymph nodes of paients with melanoma. Ann Surg 2000; 231:795-803.
20. Marincola, F. M., Jaffee, E. M., Hickun, D. J., and Ferrone, S. Escape of human solid tumors from T-cell Recognition: Molecular mechanisms and functional significance. Adv. Immunol. 74: 181-273, 2000.
21. Masuda N, Ohnishi T, Kawamoto S, Monden M, Okubo K. Analysis of chemical modification of RNA from formalin-fixed samples and optimization of molecular biology applications for such samples. Nuc Acid Res 1999; 27:4436-43.
22. Mitas M, Mikhitarian K, Walters C, et al. Quantitative real-time RT-PCR detection of breast cancer micrometastasis using a multigene marker panel. Int J Cancer 2001; 93:162-71.
23. Miyashiro, I., Kuo, C., Huynh, K., Iida A., Morton D., Bilchik, A., Giuliano A., and Hoon D. S. B. Molecular strategy for detecting metastatic cancers with use of multiple tumor-specific MAGE-A genes. Clin. Chem. 47: 505-512, 2001.

24. Morton D L, Wen D R, Foshag L J, Essner R, Cochran A. Intraoperative lymphatic mapping and selective cervical lymphadenectomy for early-stage melanomas of the head and neck. J Clin Oncol 1993; 11:1751-6.
25. Morton D L, Foshag L J, Hoon D S, Nizze J A, Famatiga E, Wanek L A, Chang C, Davtyan D G, Gupta R K, Elashoff R, Irie R. Prolongation of survival in metastatic melanoma after active specific immunotherapy with a new polyvalent melanoma vaccine. Ann Surg 1992; 216:463-82.
26. Morton D L, Barth A. Vaccine therapy for malignant melanoma. CA Cancer J Clin 1996; 46:225-44.
27. Morton D L, Thompson J F, Essner R, Elashoff R, Stern S L, Nieweg O E, et al. Validation of the accuracy of intraoperative lymphatic mapping and sentinel lymphadenectomy for early-stage melanoma: multicenter trial. Multicenter Selective Lymphadenectomy Trial Group. Ann Surg 1999; 230:453-63.
28. O'Day S J, Boasberg P D, Piro L, Kristedja T S, et al. Maintenance biotherapy for metastatic melanoma with interleukin-2 and granulocyte macrophage-colony stimulating factor improves survival for patients responding to induction concurrent biochemotherapy. Clin Cance Res 2002; 8:2775-81.
29. Rigel, D. S., Frieman, R. J., and Kopf, A. W. The incidence of malignant melanoma in the United States: issues as we approach the 21st century. J. Am. Acad. Dermatol., 34: 839-847, 1996.
30. Sarantou, T., Chi, D. D. J., Garrison, D. A., Conrad, A. J., Schmid, P. Morton, D. L., and Hoon D. S. B. Melanoma-associated antigens as messenger RNA detection markers for melanoma. Cancer Res., 57: 1371-1376, 1997.
31. Scholl F A, Kamarashev J, Murmann O V, Geertsen R, Dummer R, Schafer B W. PAX3 is expressed in human melanomas and contributes to tumor cell survival. Cancer Res 2001; 61:823-26.
32. Schultz E S, Lethe B, Cambiaso C L, et al. A MAGE-A3 peptide presented by HLA-DP4 is recognized on tumor cells by CD4+ cytolytic T lymphocytes. Cancer Res 2000; 60:6272-5.
33. Shirota Y, Stoehlmacher J, Brabender J, et al. ERCC1 and thymidylate synthase mRNA levels predict survival for colorectal cancer patients receiving combination oxaliplatin and fluorouracil chemotherapy. J Clin Oncol 2001; 19:4298-304.
34. Shivers S C, Wang X, Li W, et al. Molecular staging of malignant melanoma: correlation with clinical outcome. JAMA 1998; 280:1410-5.
35. Specht, K., Richter, T., Muller, U., Walch, A., Hofler, M. W. Quantitative gene expression analysis in microdissected archival tissue by real-time RT-PCR. J. Mol Med 78: B27, 2000.
36. Taback B, Morton D L, O'Day S J, Nguyen D H, Nakayama T, Hoon D S. The clinical utility of multimarker RT-PCR in the detection of occult metastasis in patients with melanoma. Recent Results Cancer Res 2001; 158:78-92.
37. Tai T, Paulson J C, Cahan L D, Irie R F. Ganglioside GM2 as a human tumor antigen (OFA-I-1). Proc Natl Acad Sci USA 1983; 80:5392-6.

What is claimed is:

1. A method for melanoma prognosis, comprising:
    (a) isolating nucleic acid from a sentinel lymph node (SLN) sample obtained from a first melanoma patient, wherein the SLN sample is histopathologically negative for melanoma cells;
    (b) amplifying mRNA transcripts encoded by MAGE-A3, MART-1, GalNAcT and PAX3 marker genes, the mRNA transcripts being obtained from nucleic acid from the SLN sample obtained from the first melanoma patient;
    (c) detecting levels of the mRNA transcripts encoded by the MAGE-A3, MART-1, GalNAcT and PAX3 marker genes; and
    (d) comparing levels of mRNA transcripts encoded by the MAGE-A3, MART-1, GalNAcT and PAX3 marker genes in nucleic acid from an SLN sample obtained from a second melanoma patient to levels of mRNA transcripts encoded by the MAGE-A3, MART-1, GalNAcT and PAX3 marker genes in the nucleic acid from the SLN sample obtained from the first melanoma patient to predict metastatic melanoma recurrence, metastatic melanoma-free survival, overall survival, or a combination thereof, for the first melanoma patient, higher levels of the mRNA transcripts encoded by the MAGE-A3, MART-1, GalNAcT and PAX3 marker genes in the nucleic acid from the SLN sample obtained from the first melanoma patient indicating that the first melanoma patient has an increased probability of metastatic melanoma recurrence as compared to the probability of metastatic melanoma recurrence of the second melanoma patient, a decreased probability of metastatic melanoma-free survival as compared to the probability of metastatic melanoma-free survival of the second melanoma patient, or a decreased probability of overall survival as compared to the probability of overall survival of the second melanoma patient, and lower levels of the mRNA transcripts encoded by the MAGE-A3, MART-1, GalNAcT and PAX3 marker genes in the nucleic acid from the SLN sample obtained from the first melanoma patient indicating that the first melanoma patient has a decreased probability of metastatic melanoma recurrence as compared to the probability of metastatic melanoma recurrence of the second melanoma patient, an increased probability of metastatic melanoma-free survival as compared to the probability of metastatic melanoma-free survival of the second melanoma patient, or an increased probability of overall survival as compared to the probability of overall survival of the second melanoma patient.

2. The method of claim 1 wherein the nucleic acid is mRNA and the mRNA transcripts are amplified using real-time reverse transcriptase polymerase chain reaction (qRT-PCR).

3. The method of claim 1 wherein the SLN sample is paraffin-embedded (PE) or frozen.

4. The method of claim 1, wherein histopathology of the SLN sample is determined by hematoxylin and eosin staining or immunohistochemistry.

5. The method of claim 1, wherein the first melanoma patient's prognosis is predicted for at least a three-year period following a removal of a primary tumor, sentinel lymphadenectomy (SLND), or both.

6. A method for melanoma prognosis, comprising:
  (a) isolating nucleic acid from a sentinel lymph node (SLN) sample obtained from a first melanoma patient, wherein the SLN sample is histopathologically negative for melanoma cells;
  (b) amplifying mRNA transcripts encoded by GalNAcT, PAX3, MAGE-A3 and MART-1 marker genes, the mRNA transcripts being obtained from nucleic acid from the SLN sample obtained from the first melanoma patient;
  (c) detecting levels of the mRNA transcripts encoded by the GalNAcT, PAX3, MAGE-A3 and MART-1 marker genes; and
  (d) comparing levels of the mRNA transcripts encoded by the GalNAcT, PAX3, MAGE-A3 and MART-1 marker genes in nucleic acid from an SLN sample obtained from a second melanoma patient to levels of mRNA transcripts encoded by GalNAcT, PAX3, MAGE-A3 and MART-1 marker genes in the nucleic acid from the SLN sample obtained from the first melanoma patient to determine whether the levels of mRNA transcripts encoded by the GalNAcT, PAX3, MAGE-A3 and MART-marker genes in the nucleic acid from the SLN sample obtained from the first melanoma patient are higher than the levels of mRNA transcripts encoded by the GalNAcT, PAX3, MAGE-A3 and MART-1 marker genes in the nucleic acid from the SLN sample obtained from the second melanoma patient.

7. The method of claim 6 wherein the nucleic acid is mRNA and the mRNA transcripts encoded by the marker genes are amplified using quantitative real-time reverse transcriptase polymerase chain reaction (qRT-PCR).

8. The method of claim 6 wherein the SLN sample is paraffin-embedded (PE) or frozen.

9. The method of claim 6, wherein histopathology of the SLN sample is determined by hematoxylin and eosin staining or immunohistochemistry.

10. A method for melanoma prognosis comprising:
  (a) isolating nucleic acid from a sentinel lymph node (SLN) sample obtained from a melanoma patient, wherein the SLN sample is histopathologically negative for melanoma cells;
  (b) amplifying mRNA transcripts encoded by GalNAcT, PAX3, MAGE-A3 and MART-1 marker genes by real-time reverse transcriptase polymerase chain reaction (qRT-PCR), the mRNA transcripts being obtained from nucleic acid from the SLN sample obtained from the melanoma patient; and
  (c) quantifying each of the mRNA transcripts encoded by the GalNAcT, PAX3, MAGE-A3 and MART-1 marker genes by an mRNA copy number such that a positive copy number for any of the mRNA transcripts indicates a poorer prognosis for the patient than a copy number of zero.

11. A method for melanoma prognosis comprising:
  (a) isolating nucleic acid from a sentinel lymph node (SLN) sample obtained from a melanoma patient, wherein the SLN sample is histopathologically negative for melanoma cells;
  (b) amplifying mRNA transcripts encoded by GalNAcT, PAX3, MAGE-A3 and MART-1 marker genes by real-time reverse transcriptase polymerase chain reaction (qRT-PCR), the mRNA transcripts being obtained from nucleic acid from the SLN sample obtained from the melanoma patient; and
  (c) quantifying each of the mRNA transcripts encoded by the GalNAcT, PAX3, MAGE-A3 and MART-1 marker genes by an mRNA copy number, each mRNA copy number being determined from a standard curve of known copy numbers for cDNA corresponding to each gene, a positive copy number for any of the mRNA transcripts indicating a poorer prognosis for the patient than a copy number of zero.

12. The method of claim 11 further comprising upstaging the prognosis for the patient if any copy number is greater than zero.

13. A method for melanoma prognosis in a patient, the method comprising:
  (a) isolating nucleic acid from a sentinel lymph node (SLN) sample obtained from a melanoma patient, wherein the SLN sample is histopathologically negative for melanoma cells;
  (b) amplifying mRNA transcripts encoded by GalNAcT, PAX3, MAGE-A3, and MART-1 marker genes by real-time reverse transcriptase polymerase chain reaction (qRT-PCR), the mRNA transcripts being obtained from nucleic acid from the SLN sample obtained from the melanoma patient; and
  (c) quantifying levels of the mRNA transcripts encoded by the GalNAcT, PAX3, MAGE-A3, and MART-1 marker genes by an mRNA copy number such that an mRNA copy number greater than zero indicates a poorer prognosis for the melanoma patient than a copy number of zero.

14. The method of claim 13 further comprising upstaging the prognosis for the melanoma patient if the copy number is greater than zero.

15. The method of claim 13 wherein the nucleic acid is mRNA.

16. The method of claim 13 wherein the SLN sample is paraffin-embedded (PE) or frozen.

17. The method of claim 13 wherein histopathology of the SLN sample is determined by hematoxylin and eosin staining or immunohistochemistry.

18. The method of claim 13 wherein the patient's prognosis is predicted for at least a three-year period following a removal of a primary tumor, sentinel lymphadenectomy (SLND), or both.

* * * * *

UNITED STATES PATENT AND TRADEMARK OFFICE
CERTIFICATE OF CORRECTION

PATENT NO.        : 7,910,295 B2
APPLICATION NO.   : 10/713808
DATED             : March 22, 2011
INVENTOR(S)       : Dave S. B. Hoon It is certified that error appears in the above-identified patent and that said Letters Patent is hereby corrected as shown below:

Column 29, Line 58, Claim 6:

Delete "MART-" and insert -- MART-1 --.

Signed and Sealed this
Nineteenth Day of July, 2011

David J. Kappos
*Director of the United States Patent and Trademark Office*